(12) United States Patent
Yang et al.

(10) Patent No.: US 11,332,715 B2
(45) Date of Patent: *May 17, 2022

(54) METHOD FOR CULTURING MESENCHYMAL STEM CELLS

(71) Applicant: MEDIPOST CO., LTD, Seoul (KR)

(72) Inventors: Yoon-Sun Yang, Seoul (KR); Won Il Oh, Seoul (KR); Sun Jae Kwon, Seoul (KR); Mi Yeon Lee, Seoul (KR); Hong Bae Jeon, Seoul (KR)

(73) Assignee: MEDIPOST CO., LTD, Seoul (KR)

( * ) Notice: Subject to any disclaimer, the term of this patent is extended or adjusted under 35 U.S.C. 154(b) by 472 days.

This patent is subject to a terminal disclaimer.

(21) Appl. No.: 16/370,102

(22) Filed: Mar. 29, 2019

(65) Prior Publication Data

US 2019/0218517 A1    Jul. 18, 2019

Related U.S. Application Data

(60) Division of application No. 15/403,457, filed on Jan. 11, 2017, now Pat. No. 10,294,456, which is a continuation of application No. 14/425,220, filed as application No. PCT/KR2013/007891 on Sep. 2, 2013, now Pat. No. 9,580,687.

(30) Foreign Application Priority Data

Sep. 3, 2012    (KR) ........................ 10-2012-0097193

(51) Int. Cl.
*C12N 5/0775* (2010.01)
*A61K 35/28* (2015.01)

(52) U.S. Cl.
CPC ............ *C12N 5/0665* (2013.01); *A61K 35/28* (2013.01); *C12N 2500/02* (2013.01); *C12N 2500/12* (2013.01); *C12N 2500/14* (2013.01); *C12N 2500/16* (2013.01); *C12N 2500/84* (2013.01)

(58) Field of Classification Search
None
See application file for complete search history.

(56) References Cited

U.S. PATENT DOCUMENTS

| | | |
|---|---|---|
| 2003/0143207 A1 | 7/2003 | Livesey et al. |
| 2004/0151703 A1 | 8/2004 | Ha et al. |
| 2005/0281788 A1 | 12/2005 | De Bari et al. |
| 2006/0252045 A1 | 11/2006 | Chatterjee-Kishore et al. |
| 2007/0178073 A1* | 8/2007 | Chang .................... A61K 35/51 424/93.7 |
| 2007/0275362 A1 | 11/2007 | Edinger et al. |
| 2008/0226595 A1 | 9/2008 | Edinger et al. |
| 2008/0286324 A1 | 11/2008 | Stolen et al. |
| 2010/0184218 A1 | 7/2010 | Ha et al. |
| 2012/0052577 A1 | 3/2012 | Espinosa de los Monteros et al. |
| 2013/0023048 A1 | 1/2013 | Kim et al. |

FOREIGN PATENT DOCUMENTS

| | | |
|---|---|---|
| EP | 2039758 | 3/2009 |
| JP | 2006055106 A | 3/2006 |
| KR | 2003-0069115 | 8/2003 |
| KR | 10-0494265 | 6/2005 |
| KR | 10-1243276 | 3/2013 |
| WO | 2006/022091 A1 | 3/2006 |
| WO | 2009/014272 | 1/2009 |
| WO | 2009/022091 | 2/2009 |
| WO | 2010/150094 | 12/2010 |

OTHER PUBLICATIONS

Basciano et al., "Long Term Culture of Mesenchymal Stem Cell in Hypoxia Promotes a Genetic Program Maintaining Their Undifferentiated and Multipotent Status", BMC Cell Biology 12; 12 pages, BioMed Central Ltd., United States (Mar. 2011).
Das et al., "The Role of Hypoxia in Bone Marrow-Derived Mesenchymal Stem Cells: Considerations for Regenerative Medicine Approaches", Tissue Engineering: Part B 16(2): 159-168, Mary Ann Liebert, Inc., United States (2010).
Nguyen et al., "Effects of magnesium on growth and proliferation of human embryonic stem cells", 34th Annual International Conference of the IEEE EMBS:723-726, Aug. 28-Sep. 1, 2012, Sam Diego, California, United States, IEEE Service Center, United States (Aug. 28-Sep. 1, 2012).
International Search Report and Written Opinion of the International Searching Authority for International Patent Application No. PCT/KR2013/007891, Korean Intellectual Property Office, Republic of Korea, dated Nov. 15, 2013, 8 pages.
Pittenger et al., "Multilineage Potential of Adult Human Mesenchymal Stem Cells", Science 284(5411) 143-147, American Association for the Advancement of Science, United states (1999).
Kern et al., "Comparative Analysis of Mesenchymal Stem Cells from Bone Marrow, Umbilical Cord Blood, or Adipose Tissue", Stem Cells 24(5): 1294-1301, AlphaMed Press, United States (2006).
Lazarus et al., "Ex Vivo Expansion and Subsequent Infusion of Human Bone Marrow-Derived Stromal Progenitor Cells (Mesenchymal Progenitor Cells): Implications for Therapeutic Use", Bone Marrow Transplantation 16(4): 557-564, Nature Publishing Group, England (1995).
Xu et al., "Effect of the Calcium Sensing Receptor on Rat Bone Marrow-derived mesenchymal Stem Cell Proliferation through the ERK1/2 Pathway", Mol Biol Rep 39: 7271-7279, Springer Science+Business Media B.V., The Netherlands (2012).

(Continued)

*Primary Examiner* — Emily A Cordas
(74) *Attorney, Agent, or Firm* — Sughrue Mion, PLLC

(57) ABSTRACT

Disclosed is a method for culturing mesenchymal stem cells, comprising culturing mesenchymal stem cells in a medium containing calcium in a concentration of from 2.1 to 3.8 mM and magnesium in a concentration of from 1.0 to 3.0 mM under a hypoxic condition of 2 to 5% oxygen. The culturing method can increase the population of mesenchymal stem cells even with a small number of passages by improving mesenchymal stem cells in proliferative capacity and viability. In addition, the mesenchymal stem cells prepared by the culturing method are effectively used to treat or improve a pulmonary disease.

8 Claims, 17 Drawing Sheets

Specification includes a Sequence Listing.

(56) References Cited

OTHER PUBLICATIONS

Bieback et al., Stem Cells 2009; 27:2331-2341.
Japanese Patent Office: Communication dated Jul. 18, 2017 issued in application No. 2015-529690.
Bruder et al. J Orthop Res. vol. 16, No. 2. 1998, pp. 155-162.

* cited by examiner

SEQUENCE LISTING

<160> NUMBER OF SEQ ID NOS: 8

<210> SEQ ID NO 1
<211> LENGTH: 19
<212> TYPE: DNA
<213> ORGANISM: Artificial Sequence
<220> FEATURE:
<223> OTHER INFORMATION: Forward primer for Oct4

<400> SEQUENCE: 1
caatttgcca agctcctga

```
<210> SEQ ID NO 2
<211> LENGTH: 20
<212> TYPE: DNA
<213> ORGANISM: Artificial Sequence
<220> FEATURE:
<223> OTHER INFORMATION: Reverse primer for Oct4

<400> SEQUENCE: 2
cgtttggctg aataccttcc                                                    20

<210> SEQ ID NO 3
<211> LENGTH: 20
<212> TYPE: DNA
<213> ORGANISM: Artificial Sequence
<220> FEATURE:
<223> OTHER INFORMATION: Forward primer for Nanog

<400> SEQUENCE: 3
agatgcctca cacggagact                                                    20

<210> SEQ ID NO 4
<211> LENGTH: 20
<212> TYPE: DNA
<213> ORGANISM: Artificial Sequence
<220> FEATURE:
<223> OTHER INFORMATION: Reverse primer for Nanog

<400> SEQUENCE: 4
tttgcgacac tcttctctgc                                                    20

<210> SEQ ID NO 5
<211> LENGTH: 18
<212> TYPE: DNA
<213> ORGANISM: Artificial Sequence
<220> FEATURE:
<223> OTHER INFORMATION: Forward primer for P16

<400> SEQUENCE: 5
gtggacctgg ctgaggag                                                      18

<210> SEQ ID NO 6
<211> LENGTH: 20
<212> TYPE: DNA
<213> ORGANISM: Artificial Sequence
<220> FEATURE:
<223> OTHER INFORMATION: Reverse primer for P16

<400> SEQUENCE: 6
ctttcaatcg gggatgtctg                                                    20

<210> SEQ ID NO 7
<211> LENGTH: 20
<212> TYPE: DNA
<213> ORGANISM: Artificial Sequence
<220> FEATURE:
<223> OTHER INFORMATION: Forward primer for GADPH

<400> SEQUENCE: 7
agccaccatc gctcagacac                                                    20

<210> SEQ ID NO 8
<211> LENGTH: 19
<212> TYPE: DNA
<213> ORGANISM: Artificial Sequence
<220> FEATURE:
<223> OTHER INFORMATION: Reverse primer for GADPH
```

```
<400> SEQUENCE: 8
gcccaatacg accaaatcc                                          19
```

METHOD FOR CULTURING MESENCHYMAL STEM CELLS

CROSS REFERENCE TO RELATED APPLICATIONS

This application is a Divisional of U.S. application Ser. No. 15/403,457 filed Jan. 11, 2017, now U.S. Pat. No. 10,294,456 issued May 21, 2019, which is a Continuation of U.S. application Ser. No. 14/425,220 filed Mar. 2, 2015, now U.S. Pat. No. 9,580,687 issued Feb. 28, 2017, which is a National Stage Application under 35 U.S.C. § 371 of International Application No. PCT/KR2013/007891, filed on Sep. 2, 2013, and claims the benefit of Korean Application No. 10-2012-0097193 filed on Sep. 3, 2012 in the Korean Patent Office, the disclosures of which are incorporated herein by reference in their entireties.

FIELD OF THE INVENTION

The present invention relates to a method for culturing mesenchymal stem cells with efficiency.

BACKGROUND OF THE INVENTION

The term "stem cell" is a generic name for an undifferentiated type of body cell found in tissues of embryos, fetuses and adults, which has the potential of differentiating into a diverse range of specialized cell types. Stem cells are characterized by self-renewal, the ability to go through numerous cycles of cell division (while maintaining an undifferentiated state), and potency, the capacity to differentiate into specialized cell types in response to certain stimuli (environment), and even by plasticity, the ability to cross lineage barriers and adopt the expression profile and functional phenotypes of cells that are unique to other tissues.

Stem cells may be classified according to various criteria. Potency allows the classification of stem cells: pluripotent stem cells, multipotent stem cells and unipotent stem cells. Pluripotent stem cells have pluripotency to differentiate into any type of cells. Embryonic stem cells and induced pluripotent stem cells (iPS), which have recently received intensive attention from scientists, are representative of pluripotent stem cells. Adult stem cells show multipotency or unipotency. Among them are hematopoietic stem cells, mesenchymal stem cells, neural stem cells, etc.

In spite of various attempts to utilize the pluripotency of human embryonic stem cells in cell therapeutics, the high likelihood of oncogenesis and immune rejection response still remain and are difficult obstacles to overcome.

Induced pluripotent stem cells (iPS cells) have recently been suggested as a solution to these problems. iPS cells are a type of pluripotent stem cell artificially derived from a differentiated adult somatic cell by reprogramming. iPS cells may avoid the issue of immune rejection response because they are derived entirely from the patient, however, the risk of oncogenesis with iPS cells is still a problem to be solved.

As an alternative, mesenchymal stem cells are being promoted because they exhibit immunomodulatory effects and present no risk of oncogenesis. Mesenchymal stem cells are multipotent stem cells that can differentiate into a variety of cell types, including adipocytes, osteoblasts, chondrocytes, myoblasts, neuroblasts, myocardioblasts, hepatocytes, islet beta cells, vascular cells, etc., and are known to have the function of modulating immune responses.

Mesenchymal stem cells may be isolated from various tissues such as the bone marrow, umbilical cord blood, adipose tissue, etc., but are not sufficiently defined because cell surface markers are somewhat different from one another according to the origin from which the mesenchymal stem cells are derived. On the whole, if they can differentiate into osteoblasts, chondrocytes and myoblasts, have a spindle shaped morphology, and express the surface markers CD73(+), CD105(+), CD34(−) and CD45(−), the stem cells are defined as mesenchymal stem cells. In this context, mesenchymal stem cells of different genetic origins and/or backgrounds do not significantly differ from one another in terms of their definition, i.e., that of a mesenchymal stem cell, but are typically different from each other in terms of in vivo activity. Further, when mesenchymal stem cells are used as exogenous cell therapeutics, a limited pool of mesenchymal stem cells does not allow many choices or available options, even in spite of low in vivo activity.

In addition, the minimum number of mesenchymal stem cells necessary for them to be used as a cell therapeutic in regenerative medicine and/or cell therapy is approximately $1\times10^9$ cells. In practice, the minimum number is further increased in consideration of experiments for setting proper conditions and determining criteria. The supply of mesenchymal stem cells in such quantities from various origins requires at least ten in vitro passages. In this case, however, the cells become aged and deformed so that they may be unsuitable for use as cell therapeutics.

Thus, a culturing method effective for the mass production of mesenchymal stem cells is required.

Methods for culturing mesenchymal stem cells are described in Korean Patent Laid-Open Publication No. 2003-0069115, and literature [Pittinger M F et al. *Science*, 284: 143-7, 1999; Lazarus H M et al. *Bone Marrow Transplant*, 16: 557-64, 1995; and Kern et al., *Stem Cells*, 24: 1294-1301, 2006], but difficulties were found in guaranteeing the number of cells available for mass production. In addition, these methods suffer from the disadvantage of a decreasing number of mesenchymal stem cells in proliferative capacity every passage. For example, umbilical cord blood-derived mesenchymal stem cells cannot proliferate, but are rapidly aged after 9~10 passages, and this phenomenon is found after 5~6 passages in bone marrow- or lipid-derived mesenchymal stem cells. Therefore, there is a need for a novel method by which the number of mesenchymal stem cells can be increased to the extent sufficient for industrial applicability with higher simplicity and economical benefit compared to conventional methods.

SUMMARY OF THE INVENTION

It is therefore an object of the present invention to provide a method for culturing mesenchymal stem cells with efficiency.

It is another object of the present invention to provide mesenchymal stem cells, prepared by the method, that exhibit excellent proliferative capacity and immunological properties.

It is a further object of the present invention to provide a cell therapeutic agent comprising the mesenchymal stem cells.

In accordance with one aspect of the present invention, there is provided a method for culturing mesenchymal stem cells, comprising culturing mesenchymal stem cells in a medium containing calcium in a concentration of from 2.1 to 3.8 mM and magnesium in a concentration of from 1.0 to 3.0 mM under a hypoxic condition with a 2~5% oxygen concentration.

In accordance with another aspect of the present invention, there is provided mesenchymal stem cells, prepared by the method, which are improved in proliferative capacity, viability, recovery rate, and immune property.

In accordance with further aspect of the present invention, there is provided a cell therapeutic agent comprising the mesenchymal stem cells of the present invention.

The culturing method of the present invention can increase the population of mesenchymal stem cells even at a small number of passages by improving mesenchymal stem cells in proliferative capacity and viability. In addition, the mesenchymal stem cells prepared by the culturing method of the present invention are effectively used not only as a safe cell therapeutic agent due to their lacking immunogenicity, but also as a cartilage regenerating medicine owing to their excellent secretion of cytokines.

BRIEF DESCRIPTION OF DRAWINGS

In FIG. 1A and FIG. 1C, P1 to P3 represent numbers of passage.

In FIG. 3A and FIG. 3C, P1 to P3 represent numbers of passage.

DETAILED DESCRIPTION OF THE INVENTION

Figure 1A:
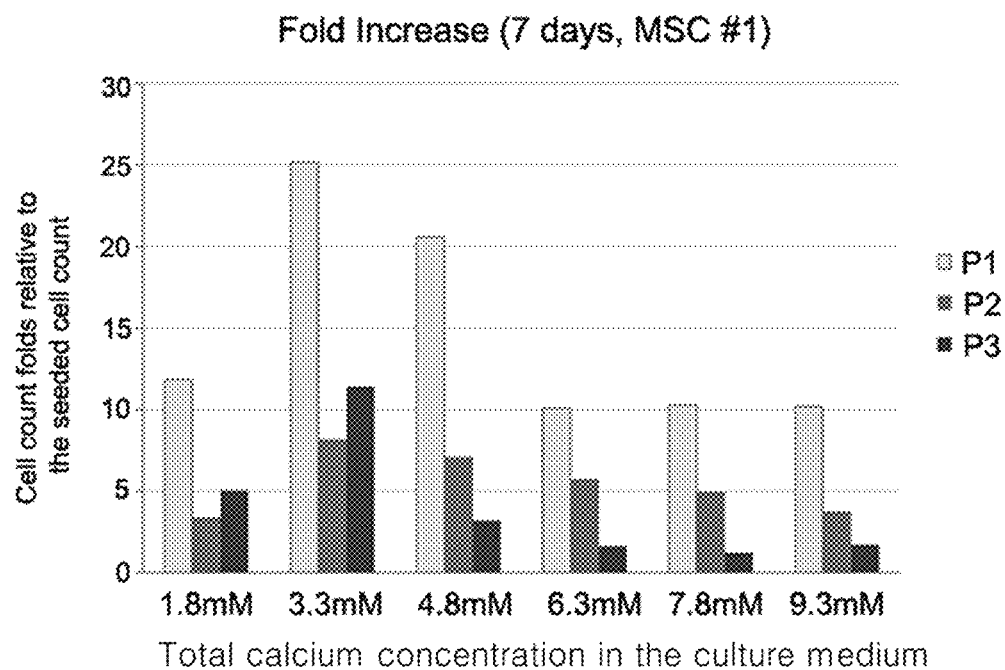
FIG. 1A, FIG. 1B, FIG. 1C, and FIG. 1D are graphs showing cell count folds relative to the seeded cell count at 7 days (FIG. 1A and FIG. 1C) and cumulative cell counts until 21 days (FIG. 1B and FIG. 1D) after umbilical cord blood-derived mesenchymal stem cells derived from two different sources (MSC #1 and #2) were cultured in α-MEM ranging in calcium concentration from 1.8 to 9.3 mM.
Figure 1B:
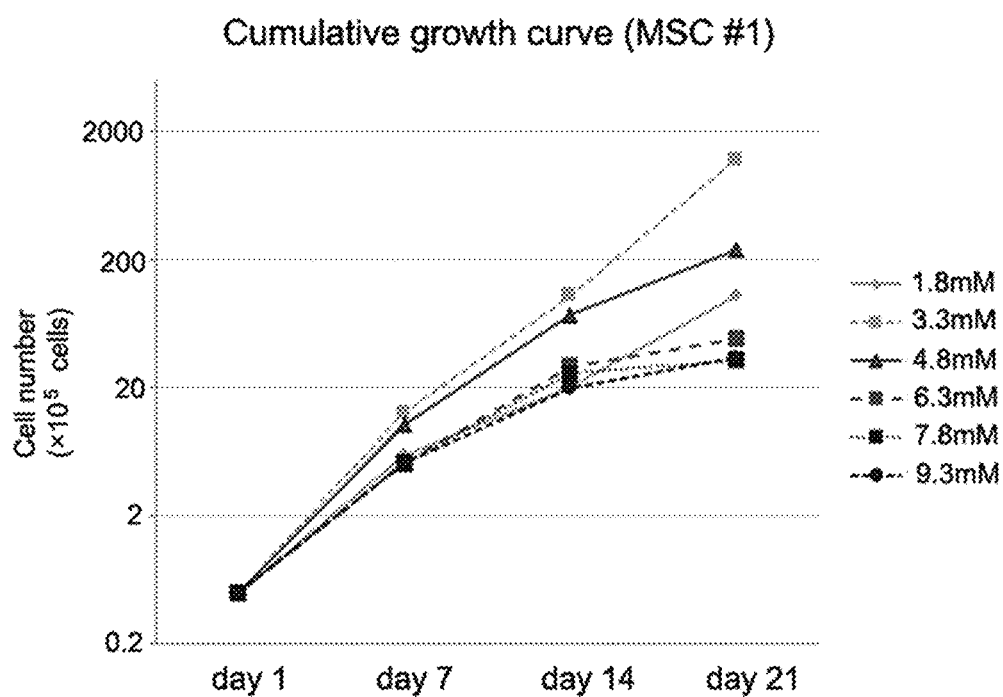
Figure 1C:
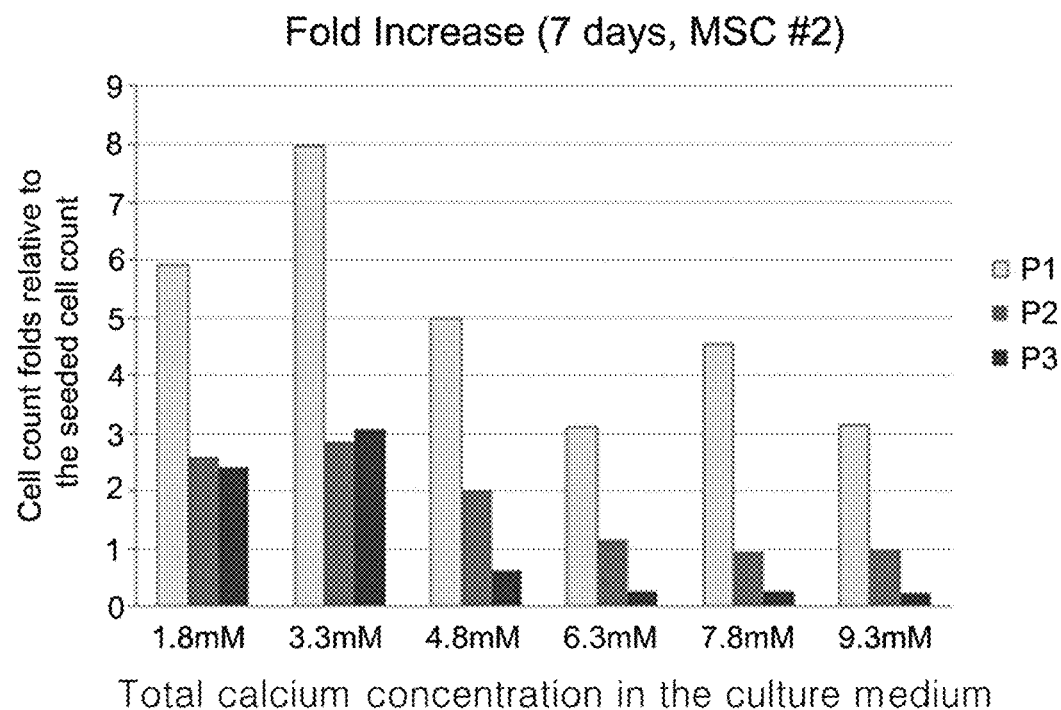

In accordance with a preferred embodiment, the present invention provides a method for culturing mesenchymal stem cells, comprising culturing mesenchymal stem cells in a medium containing calcium in a concentration of from 2.1 to 3.8 mM and magnesium in a concentration of from 1.0 to 3.0 mM under a hypoxic condition of 2 to 5% oxygen.

The culturing method of the present invention may be applied to mesenchymal stem cells of various origins. Examples of the mesenchymal stem cells useful in the present invention include those derived from umbilical cord blood, bone marrow, lipid, muscle, skin, amniotic fluid, umbilical cord, or teeth, but are not limited thereto. In one preferred embodiment of the present invention, the culturing method of the present invention is applied to umbilical cord blood-derived mesenchymal stem cells.

In addition, the mesenchymal stem cells to which the culturing method of the present invention can be applied may be derived from various subjects. For example, the mesenchymal stem cells useful in the present invention may be obtained from mammals including humans, but are not limited thereto. In one preferred embodiment of the present invention, mesenchymal stem cells of human origin are used.

The culturing method of the present invention is primarily characterized by the use of a culture medium containing calcium in a concentration of from 2.1 to 3.8 mM, and magnesium in a concentration of from 1.0 to 3.0 mM. The culture medium may be prepared from a typical culture medium for stem cells by adjusting the concentrations of calcium and magnesium. Examples of the typical culture medium include Dulbecco's modified eagle medium (DMEM), minimal essential medium (MEM), α-MEM, McCoys 5A medium, eagle's basal medium, CMRL (Connaught Medical Research Laboratory) medium, Glasgow minimal essential medium, Ham's F-12 medium, IMDM (Iscove's modified Dulbecco's medium), Leibovitz's L-15 medium, RPMI (Roswell Park Memorial Institute) 1640 medium, medium 199, and Hank's medium 199, but are not limited thereto.

Optionally, the culture medium may or may not contain serum. In addition, a serum replacement may be used, instead of serum, in the culture medium.

In one embodiment of the present invention, the culture medium contains 5 to 30% of fetal bovine serum (FBS). In another embodiment, the culture medium contains a serum replacement. In addition to a commercially available product, various growth factors in a human serum or a human platelet lysate, including PDGF, TGF, IGF, and cytokines of a family of such proteins may be used as the serum replacement.

In the culturing method of the present invention, calcium functions to promote the proliferation of mesenchymal stem cells, with the suppression of immunogenicity and the stimulation of cytokine secretion. In this regard, calcium may be used in a concentration of from 2.1 to 3.8 mM in the medium, preferably in a concentration of from 3.3 to 3.8 mM, and more preferably in a concentration of approximately 3.6 mM. For instance, when α-MEM is adopted as the culture medium, calcium may be added in a concentration of from 0.3 to 2.0 mM, preferably in a concentration of from 1.5 to 2.0 mM, and more preferably in a concentration of approximately 1.8 mM because the medium already contains 1.8 mM of calcium. Likewise, the calcium concentration to be added to achieve the desired concentration necessary for implementing the culturing method of the present invention can be readily calculated in consideration of the calcium concentration of a medium itself, taken from among typical media.

In the culture medium of the present invention, magnesium is employed to prevent the precipitation of calcium. Magnesium may be used in a concentration of from 1.0 to 3.0 mM in the medium, and preferably in a concentration of approximately 1.8 mM. For example, when magnesium is present in a concentration of less than 1.0 mM in the culture medium, calcium is apt to precipitate. On the other hand, a magnesium concentration higher than 3.0 mM in the culture medium is likely to block the formation of the extracellular matrix (ECM), interfere with the adherence of the cells to the bottom of the culture dish, thus rendering them susceptible to shear stress, and increase intracellular mineralization. For instance, when α-MEM is adopted as the culture medium, magnesium may be added in a concentration of from 0.2 to 2.2 mM, and preferably in a concentration of 1.0 mM because the medium already contains 0.8 mM magnesium. Likewise, the magnesium concentration to be added to achieve the desired concentration necessary for implementing the culturing method of the present invention can be readily calculated in consideration of the magnesium concentration of a medium itself, taken from among typical media.

Thus, the culture medium according to a preferred embodiment of the present invention may be based on α-MEM supplemented with 5 to 30% of fetal bovine serum (FBS), 0.3 to 2.0 mM of calcium, and 0.2 to 2.2 mM of magnesium, thus calcium and magnesium amounting to a total of from 2.1 to 3.8 mM, and from 1.0 to 3.0 mM, respectively.

Furthermore, another feature of the culturing method of the present invention is a hypoxic culturing condition for mesenchymal stem cells. Compared to a normoxic condition, the hypoxic condition promotes the proliferation of mesenchymal stem cells, with the suppression of immunogenicity and the stimulation of cytokine secretion. In this context, the hypoxic condition is an atmosphere with an oxygen content of from 2 to 5%. A problem with an oxygen concentration below 2% or over 5% is a significant decrease in the proliferation of mesenchymal stem cells. In one preferred embodiment of the present invention, mesenchymal stem cells are cultured in an atmosphere of approximately 3% oxygen. The hypoxic condition may be achieved by adjusting the oxygen concentration of a cell incubator. For example, an incubator may be purged with nitrogen (100%) or nitrogen/carbon dioxide (95%/5%) to adjust the normoxic atmosphere into a hypoxic atmosphere. The oxygen concentration in an incubator may be monitored by an oxygen sensor installed on the incubator.

Except for the aforementioned conditions of the present invention, mesenchymal stem cells may be cultured in a conventional manner. For example, mesenchymal stem cells may be cultured in a three-dimensional bioreactor or spinner or a typical adherent culture vessel.

When the primary feature for the concentration of calcium and magnesium is combined with the secondary feature for the hypoxic condition, a synergistic effect can be obtained. That is, a combination of the concentration of calcium and magnesium and the hypoxic condition allows mesenchymal stem cells to proliferate more efficiently, with a higher improvement in the suppression of immunogenicity and the stimulation of cytokine secretion, compared to the individual conditions. For example, under the combined conditions, mesenchymal stem cells proliferate 1.5- to 5-fold further, with a 1- to 3-fold decrease in immunogenicity, and a 1.5- to 3-fold increase in cytokine secretion, compared to individual conditions. The combined condition for the culturing method of the present invention is referred to as "CMH condition" (calcium+magnesium+hypoxia condition).

The culturing method of the present invention may be applied to passages of mesenchymal stem cells. In other words, the mesenchymal stem cells cultured using the culturing method of the present invention can be sub-cultured in the same manner. By allowing mesenchymal stem cells to proliferate more efficiently, the culturing method of the present invention has the advantage of producing a greater number of mesenchymal stem cells even though fewer passages are performed. For instance, after 5 passages in which the same number of cells were inoculated and cultured for a uniform duration at each passage, the culturing method of the present invention was found to produce mesenchymal stem cells 100- to 1,000-fold greater in number than that of conventional methods.

In addition, the mesenchymal stem cells grown by the culturing method of the present invention are not only non-immunogenic so that they cause no immune responses, but can also be effectively used as a cell therapeutic agent or cartilage regenerating agent for humans.

Thus, contemplated in accordance with another aspect of the present invention are mesenchymal stem cells, prepared using the culturing method, that are improved in proliferative capacity, viability, recovery rate, and immunological property. The improvement in immunological property includes non-immunogenicity, the release of an immunosuppressant (e.g., $PGE_2$) to suppress immunity, and the increased release of useful cytokines (e.g., Tsp-2).

In accordance with a further preferred embodiment, the present invention provides a cell therapeutic agent comprising the mesenchymal stem cells. The cell therapeutic agent of the present invention finds applications in the regeneration or protection of adipocytes, osteocytes, chondrocytes, myocytes, neurocytes, cardiomyocytes, hepatocytes, islet beta cells, vascular cells, or pneumocytes. In addition, the cell therapeutic agent of the present invention is useful for one selected from the group consisting of the treatment of pulmonary diseases; the suppression or treatment of lung disease-induced inflammation; the regeneration of pulmonary tissues; and the suppression of pulmonary fibrosis. Particularly, it can be used to suppress or improve pulmonary disease-induced inflammation and fibrosis. Further, the cell therapeutic agent of the present invention can be applied to the therapy of cardiovascular diseases or the regeneration of cartilage. Moreover, the cell therapeutic agent of the present invention can reduce immune responses, immune cell penetration, or immunogenicity; improve immunomodulative functions; and suppress inflammatory reactions. Also, the cell therapeutic agent of the present invention is applied to therapy of autoimmune diseases, or graft-vs-host diseases.

The following Examples are provided to illustrate preferred embodiments of the present invention, and are not intended to limit the scope of the present invention.

For use in the present invention, human cord blood-derived mesenchymal stem cells were obtained from Medipost Co. Ltd., Korea. The cells may be prepared by collecting umbilical cord blood, isolating mesenchymal stem cells from umbilical cord blood, and culturing the mesenchymal stem cells, as illustrated below.

Umbilical cord blood may be collected from the umbilical vein which is expelled out of the uterus either while the placenta remains within the uterus after normal spontaneous vaginal delivery or once the placenta has been expelled from the uterus after cesarean section.

After neonatal birth, the umbilical vein which is expelled from the uterus and by which the newborn is connected to the placenta must be aseptically treated before collecting umbilical cord blood therefrom.

Umbilical cord blood is withdrawn from the umbilical vein into a bag containing an anticoagulant through a syringe.

Methods of isolating mesenchymal stem cells from umbilical blood and culturing the cells are disclosed in Korean Patent No. 10-0494265, and many reports (Pittinger M F, Mackay A M, et al., *Science,* 284: 143-7, 1999; Lazarus H M, Haynesworth S E, et al., *Bone Marrow Transplant,* 16: 557-64, 1995). One of them is briefly described below.

Monocytes are separated by centrifuging the collected umbilical cord blood and washed several times to remove impurities therefrom. Then, the monocytes are seeded at a proper density into a culture vessel and allowed to grow with the formation of a single layer. Mesenchymal stem cells are morphologically homogeneous and grow while forming colonies comprising spindle-shaped cells, as observed under a phase-contrast microscope. Then, the cells are cultured with passage upon confluence until a necessary number of cells are obtained.

Example 1: Proliferative Capacity of Umbilical Cord Blood-Derived Mesenchymal Stem Cells According to Calcium Concentration To examine the proliferative capacity thereof according to calcium concentration, umbilical cord blood-derived mesenchymal stem cells were cultured in the presence of various concentrations of calcium.

Umbilical cord blood-derived mesenchymal stem cells (MSC #1 and #2) which had been collected after delivery with the informed consent of different mothers and stored in a frozen state were thawed, and cultured at 37° C. in α-MEM (Invitrogen, USA) supplemented with 10% FBS under a 5% $CO_2$ condition in an incubator (hypoxia/$CO_2$ incubator, Thermo Scientific #3131). When the cells were grown to 80~90% confluency, they were separated into single cells by treatment with trypsin. To α-MEM (supplemented with 10% FBS; containing 1.8 mM calcium and 0.8 mM magnesium), various concentrations (0 mM, 1.5 mM, 3 mM, 4.5 mM, 6 mM, and 7.5 mM) of calcium were added so that the calcium concentrations of the medium was adjusted into: 1.8 mM, 3.3 mM, 4.8 mM, 6.3 mM, 7.8 mM, and 9.3 mM. The mesenchymal stem cells were inoculated at a density of 5,000 cells/$cm^2$ into the media. In order to prevent calcium-induced precipitation, magnesium was added in a concentration of 1 mM to each medium (containing a total magnesium concentration of 1.8 mM). The cells were cultured in a 21% (v/v) oxygen (normoxia) condition, with passages upon 80~90% confluency. They were counted every passage, using a CELLOMETER® Auto T4 cell counter (Nexelcom, Lawrence, Mass., USA). The results are given in FIG. 1A through FIG. 1D. FIG. 1A, FIG. 1B, FIG. 1C, and FIG. 1D are graphs showing cell count folds relative to the seeded cell count at 7 days (FIG. 1A and FIG. 1C) and cumulative cell counts until 21 days (FIG. 1B and FIG. 1D) after umbilical cord blood-derived mesenchymal stem cells derived from two different sources (MSC #1 and #2) were cultured in α-MEM to which calcium was further added in various concentrations of from 0 to 7.5 mM.

Figure 1D:
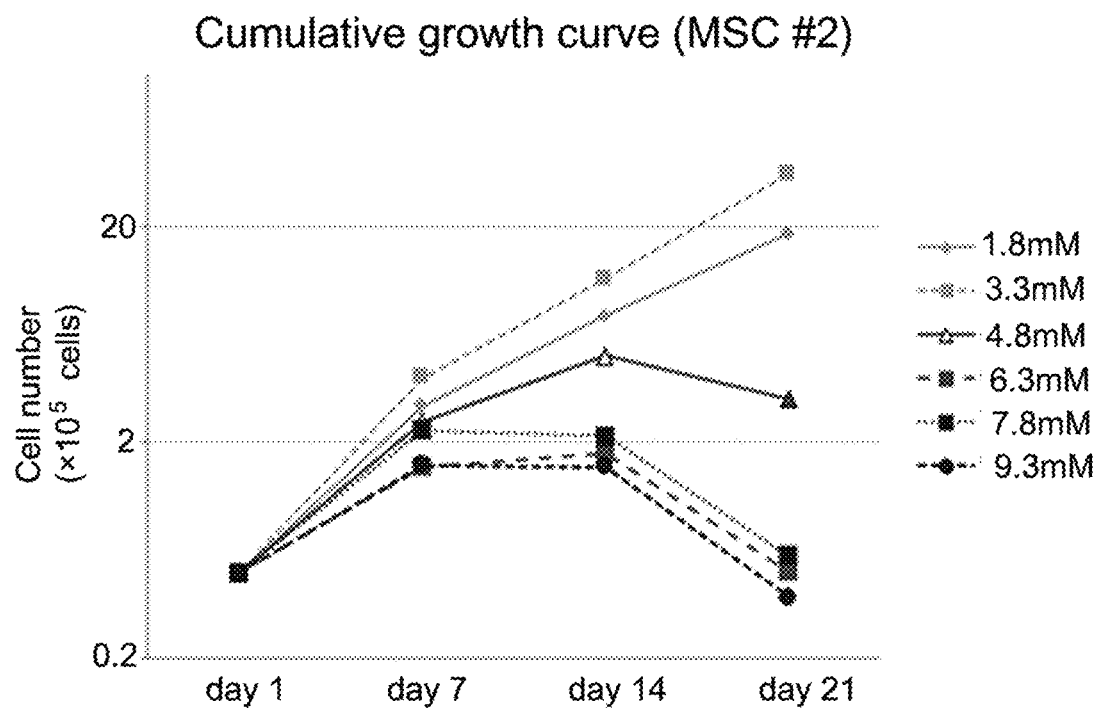

As can be seen in FIG. 1A, through FIG. 1D, the proliferative capacity of the cells peaked when calcium was further added in a concentration of 1.5 mM (a total calcium concentration of 3.3 mM), which was also observed in the same pattern over passages. Upon the addition of 3 mM or higher calcium (a total calcium concentration of 4.8 mM or higher in media), the proliferative capacity was gradually decreased.

Figure 2A:
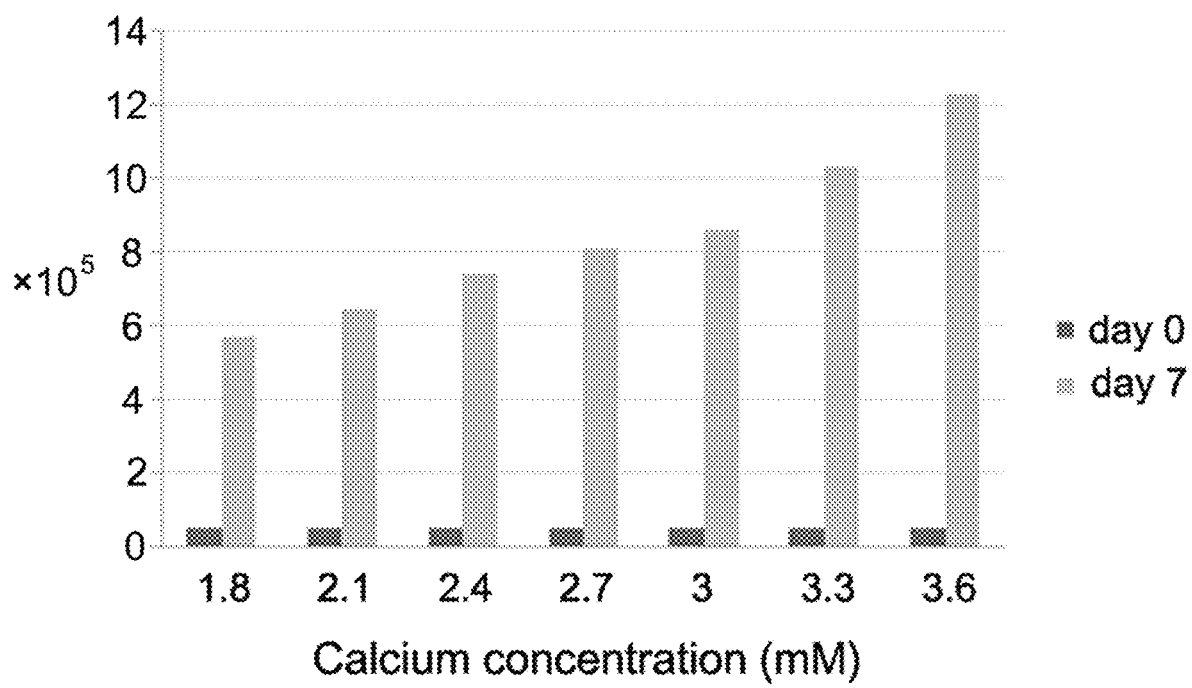
FIG. 2A, FIG. 2B, FIG. 2C, and FIG. 2D are graphs showing cell counts after umbilical cord blood-derived mesenchymal stem cells derived from two different sources (MSC #1 and #2) were cultured for 7 days in the presence of a total calcium concentration of from 1.8 to 3.6 mM (FIG. 2A and FIG. 2C) and for 6 days in the presence of a total calcium concentration of from 1.8 mM to 4.4 mM (FIG. 2B and FIG. 2D).
Figure 2B:
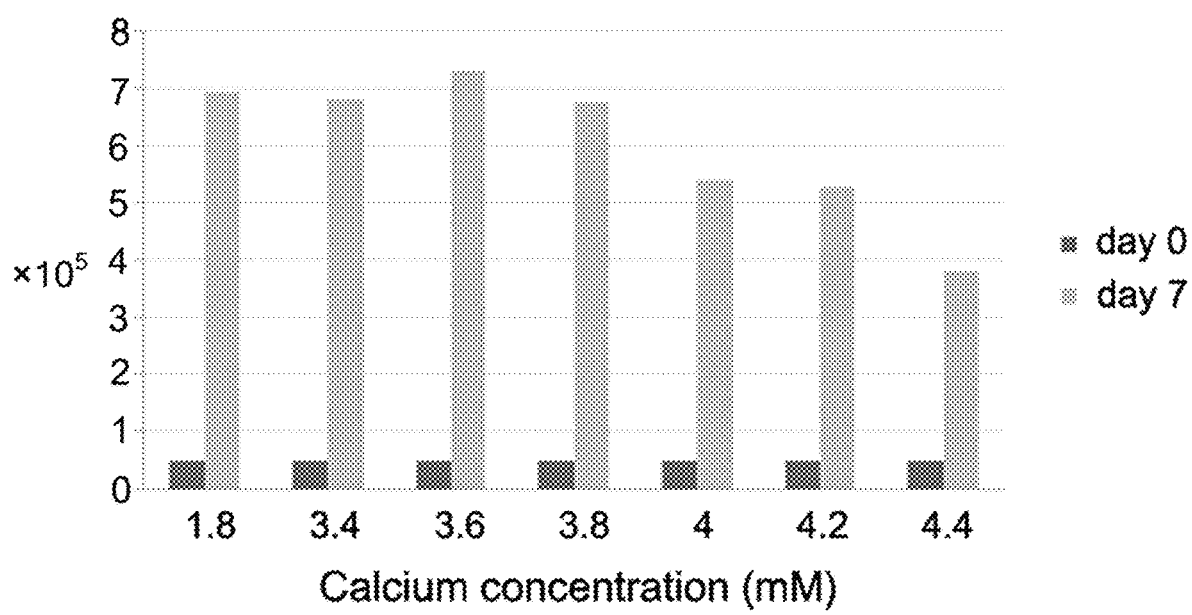
Figure 2C:
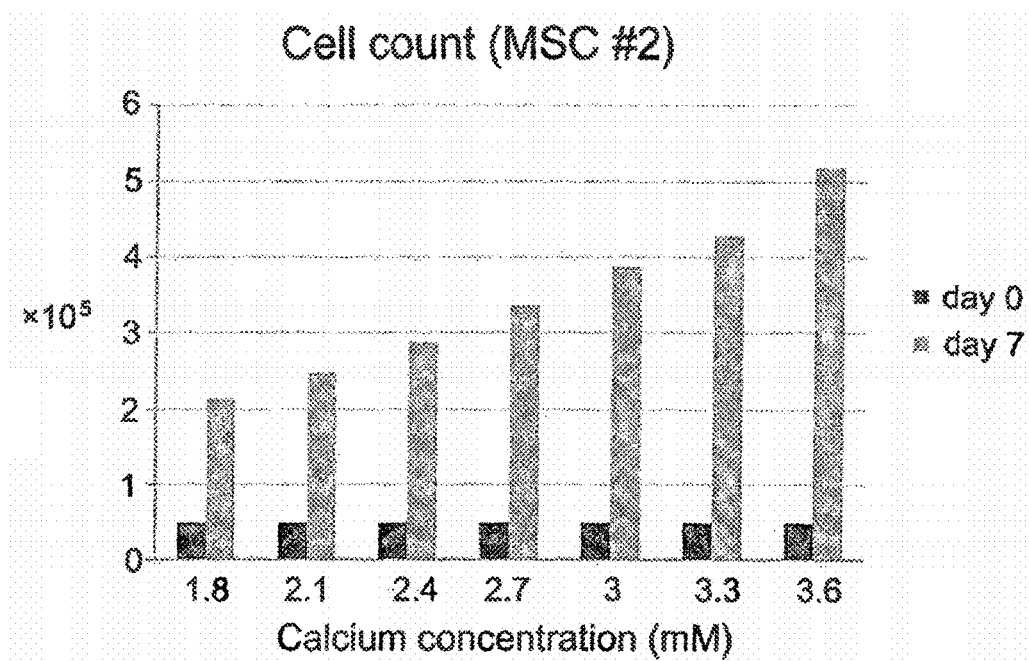
Figure 2D:
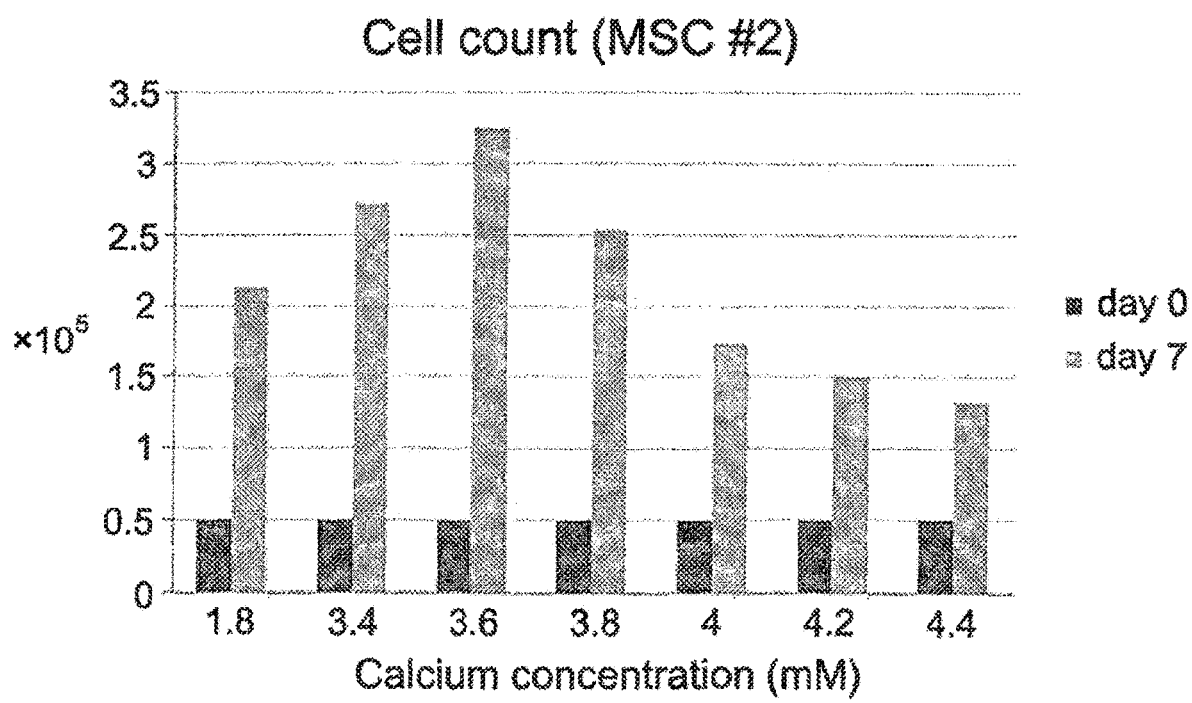

In order to determine an optimal calcium concentration, calcium was added in further fractioned concentrations to the maximum of 3 mM. The results are shown in FIG. 2A through FIG. 2D. FIG. 2A, FIG. 2B, FIG. 2C, and FIG. 2D are graphs showing cell counts after umbilical cord blood-derived mesenchymal stem cells derived from two different sources (MSC #1 and #2) were cultured for 7 days in the presence of a total calcium concentration of 1.8 mM, 2.1 mM, 2.4 mM, 2.7 mM, 3.0 mM, 3.3 mM and 3.6 mM (FIG. 2A and FIG. 2C), and for 6 days in the presence of a total calcium concentration of 1.8 mM, 3.4 mM, 3.6 mM, 3.8 mM, 4.0 mM, 4.2 mM, and 4.4 mM (FIG. 2B and FIG. 2D).

As can be seen in the graphs, the proliferative capacity increased over an added calcium concentration range from 0 to 1.8 mM (total concentrations of from 1.8 to 3.6 mM in media), and then started to decrease when the added calcium concentration exceeded 1.8 mM (a total calcium concentration of 3.6 mM in media). From these results, it is understood that the optimal calcium concentration for allowing the maximal proliferation of mesenchymal stem cells is 3.6 mM in a medium. Thus, it is advantageous in terms of proliferative capacity that mesenchymal stem cells are cultured in a typical medium containing calcium preferably in a concentration of from 2.1 to 4.3 mM, and more preferably in a concentration of from 3.3 to 3.8 mM.

Example 2: Proliferative Capacity of Umbilical Cord Blood-Derived Mesenchymal Stem Cells According to Oxygen Concentration To examine the proliferative capacity thereof according to oxygen concentration, umbilical cord blood-derived mesenchymal stem cells were cultured in the presence of various concentrations of oxygen.

Figure 3A:
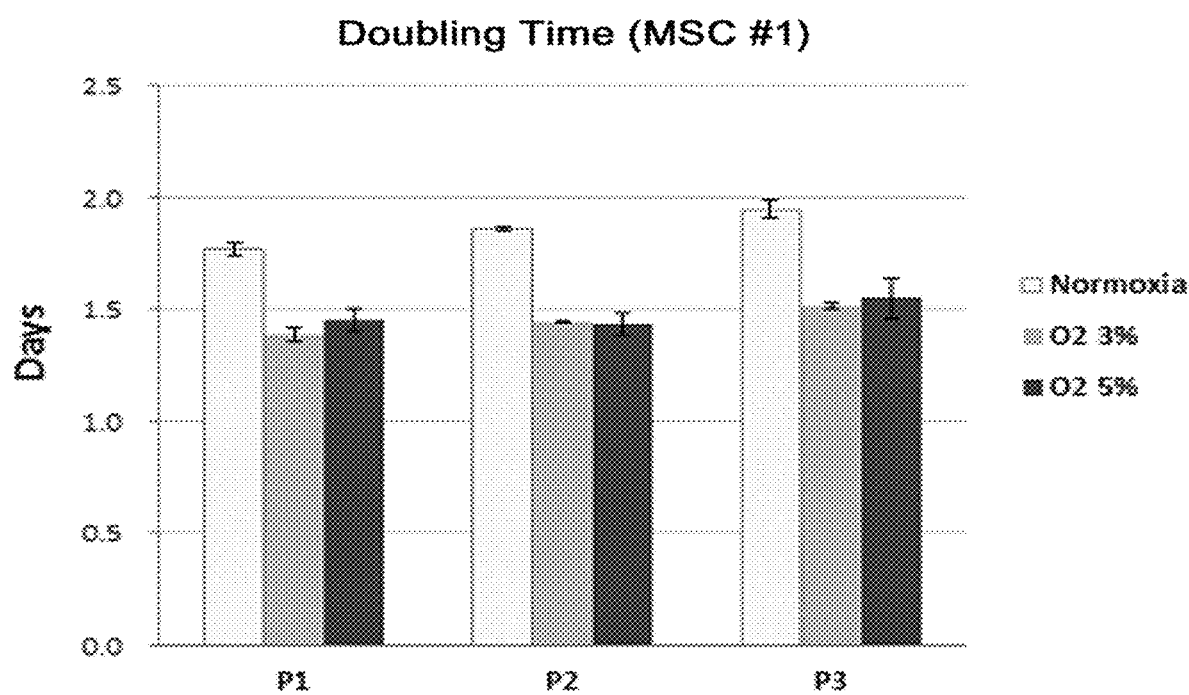
FIG. 3A, FIG. 3B, FIG. 3C, and FIG. 3D are graphs showing doubling times when umbilical cord blood-derived mesenchymal stem cells derived from two different sources (MSC #1 and #2) were cultured under various oxygen conditions (normal, 3% and 5%) (FIG. 3A and FIG. 3C), and cumulative cell counts until 21 days after the umbilical cord blood-derived mesenchymal stem cells were cultured under the oxygen conditions (FIG. 3B and FIG. 3D).
Figure 3B:
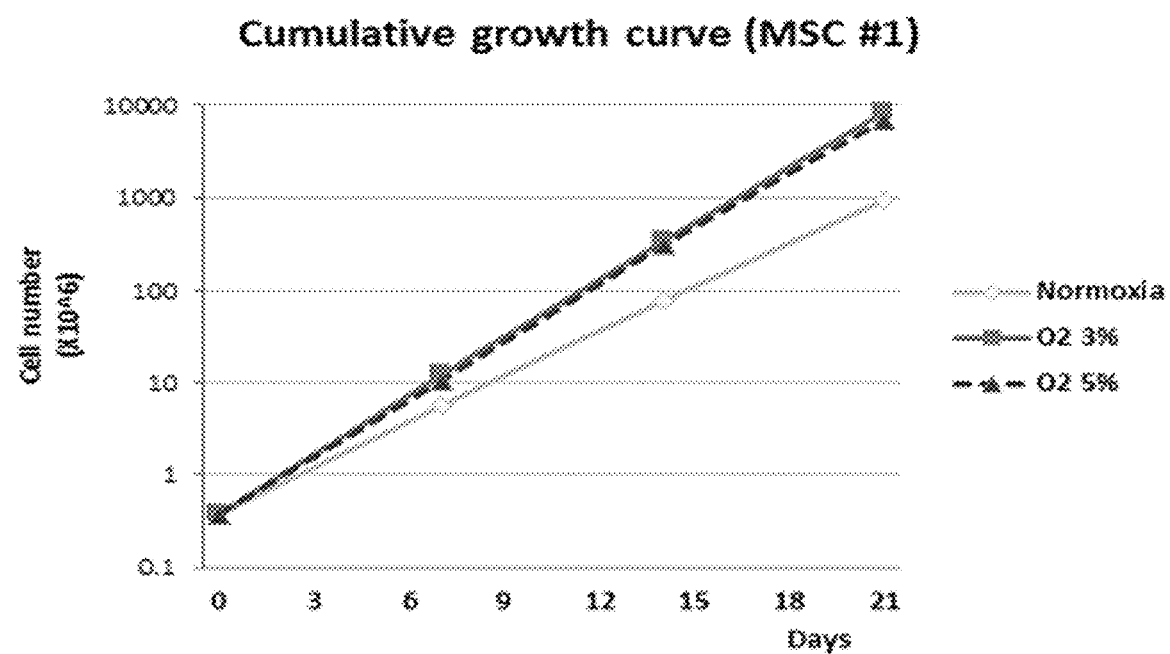
Figure 3C:
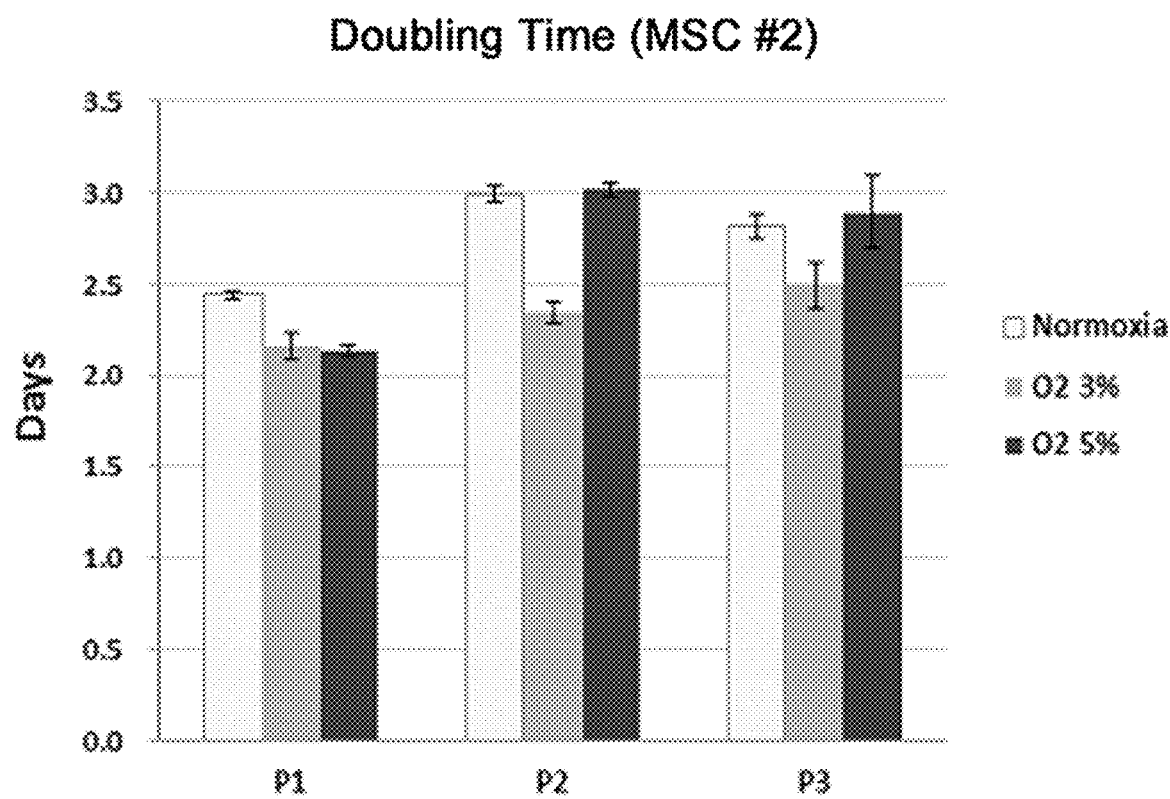
Figure 3D:
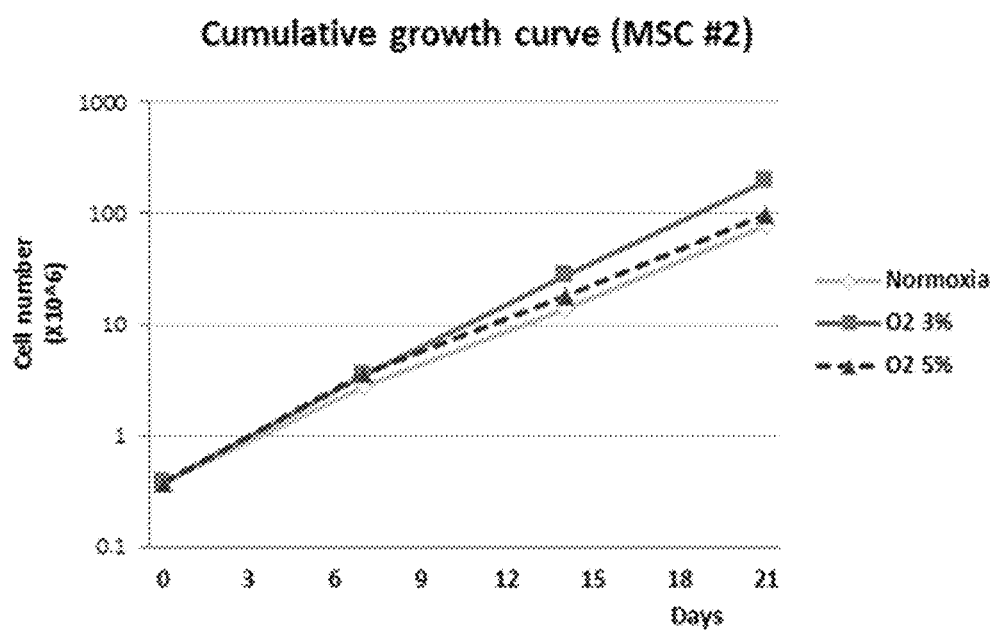

Specifically, umbilical cord blood-derived mesenchymal stem cells were cultured in the same manner as in Example 1 under 3% or 5% oxygen, or under a normoxic (oxygen level 21% in air) condition, with the exception that neither calcium nor magnesium was further added to a 10% FBS-supplemented α-MEM. The results are given in FIG. 3A through FIG. 3D. FIG. 3A, FIG. 3B, FIG. 3C, and FIG. 3D are graphs showing times it took for the cells to double in number when umbilical cord blood-derived mesenchymal stem cells derived from two different sources (MSC #1 and #2) were cultured under various oxygen conditions (normal, 3% and 5%) after 1, 2 and 3 rounds of passage (FIG. 3A and FIG. 3C), and cumulative cell counts until 21 days after the umbilical cord blood-derived mesenchymal stem cells were cultured under the oxygen conditions (FIG. 3B and FIG. 3D).

As can be seen in these graphs, the proliferative capacity was measured to be higher under the hypoxic conditions than the normoxic conditions, although there were differences between batches. Particularly, the proliferative capacity peaked at an oxygen level of 3%, which was observed in the same pattern for the cells which had been cultured with many rounds of passage. In addition, the cells were examined for proliferative capacity under further fractioned oxygen conditions to a maximum of 5%. An oxygen level of from 2 to 5% was preferred (data not shown).

Example 3: Proliferative Capacity of Umbilical Cord Blood-Derived Mesenchymal Stem Cells According to Combination of Calcium (Inclusive of Magnesium) and Oxygen Conditions An examination was made of the proliferative capacity of umbilical cord blood-derived mesenchymal stem cells according to combinations of calcium (inclusive of magnesium) and oxygen concentration conditions. The cells were cultured in a typical condition (control), in the presence of externally added calcium (inclusive of magnesium), in a hypoxic condition, and in an externally added calcium (inclusive of magnesium)/hypoxia condition (hereinafter referred to as "CMH"). In this regard, the media contained calcium and magnesium at total concentrations of 3.6 and 1.8 M, respectively (1.8 mM calcium and 1 mM magnesium additionally added). The hypoxic condition was set forth at an oxygen level of 3%. The cells were cultured in a manner similar to that of Example 1. After 5 passages (P5) in a typical condition, the mesenchymal stem cells were cultured with 7 rounds of passages (P12) in the CMH condition at regular intervals of 7 days between passages.

Figure 4A:
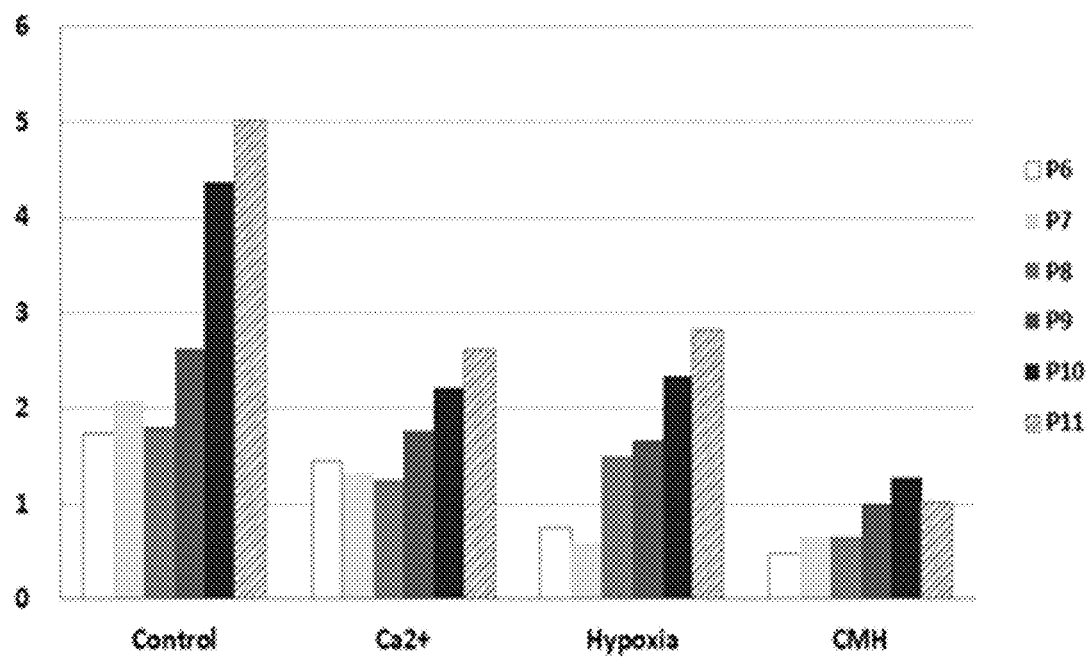
FIG. 4A and FIG. 4B show doubling times (FIG. 4A), and cumulative cell counts (FIG. 4B) after umbilical cord blood-derived mesenchymal stem cells (MSC #1) were cultured in a typical condition (control), in an increased calcium condition ($Ca^{2+}$), in a hypoxic condition, and in a CMH condition. In each of FIG. 4A and FIG. 4B, P5 to P12 represent numbers of passage, and the CMH condition means a combination of the calcium and magnesium addition condition and the hypoxic condition.
Figure 4B:
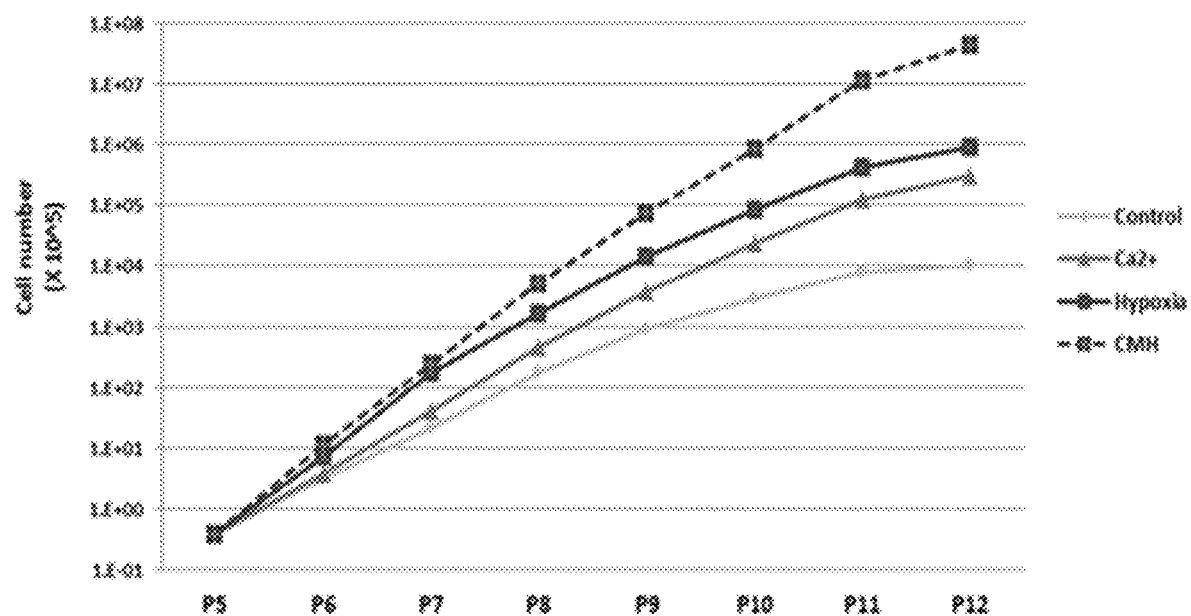

The results are given in FIG. 4A and FIG. 4B. FIG. 4A and FIG. 4B show doubling times (day) of the cells (FIG. 4A), and cumulative cell counts (FIG. 4B) after passages under the conditions.

As is understood from the data of FIG. 4A and FIG. 4b, the proliferative capacity of the cells was significantly increased when they were cultured in the CMH condition, compared to a hypoxic condition or a calcium addition condition. This effect was observed in the same pattern over many rounds of passage. Experiments with various batches of cells showed similar results although there were differences to some degree. Thus, these results demonstrate that the CMH condition of the present invention is very effective for proliferating umbilical cord blood-derived mesenchymal stem cells.

Example 4: Viability and Recovery Rate of Umbilical Cord Blood-Derived Mesenchymal Stem Cells According to Culture Condition An examination was made of the effect of the CMH condition of the present invention on the viability and recovery rate of umbilical cord blood-derived mesenchymal stem cells. For this, umbilical cord blood-derived mesenchymal stem cells (MSC #1) were cultured in a typical condition (control), in a hypoxic condition (3%), in an increased calcium condition (1.8 mM; a total calcium level of 3.6 mM in a medium), and in a CMH condition (3% $O_2$+1.8 mM calcium added+1 mM magnesium added), detached from culture vessels, and washed three times with and suspended in a fundamental medium (α-MEM). While being maintained at room temperature, the cell suspensions were examined for viability and recovery rate with time. Cell viability was expressed as a percentage of live cells to dead cells after the cells collected and suspended in a fundamental medium were stained with trypan blue and total cells including live cells stained blue in a predetermined volume (10~20 μL) of the suspension were counted using a hemocytometer. The recovery rate was expressed as a percentage of live cell counts post-culture to pre-culture.

The results are given in FIG. 5. FIG. 5 shows cell viability (upper graph) and recovery rates (lower graph) one and two days after umbilical cord blood-derived mesenchymal stem cells were cultured in the conditions.

Figure 5A:
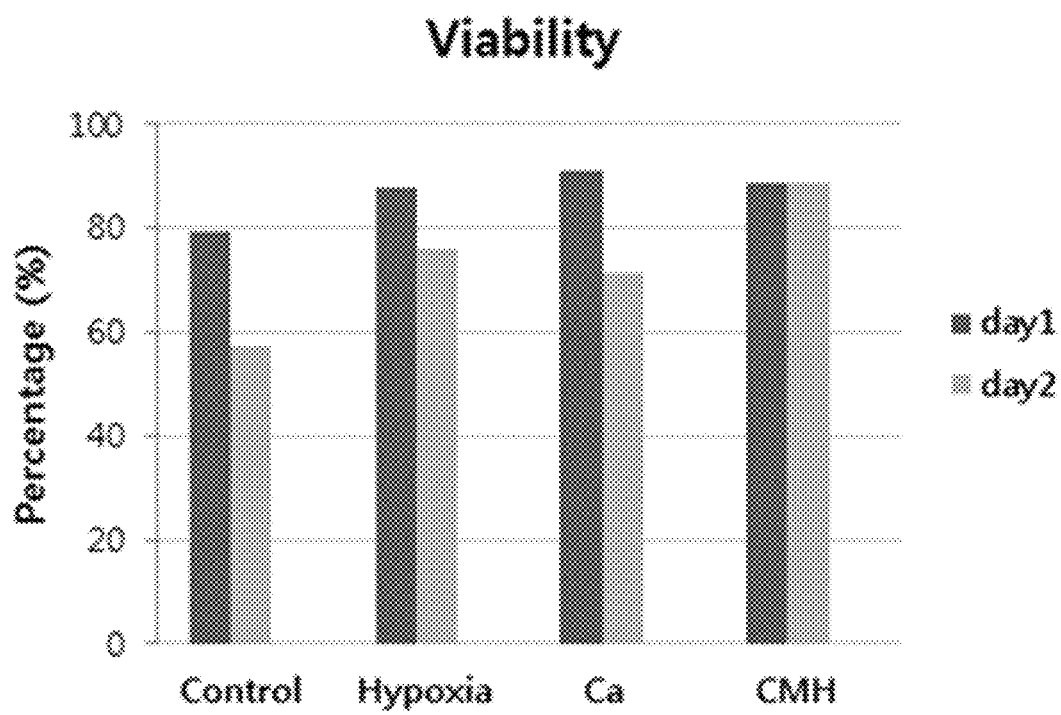
FIG. 5A and FIG. 5B show cell viability (FIG. 5A) and recovery rates (FIG. 5B) 1 and 2 days after umbilical cord blood-derived mesenchymal stem cells were cultured in a typical condition (control), in a calcium addition condition ($Ca^{2+}$), in a hypoxic condition, and in a CMH condition.
Figure 5B:
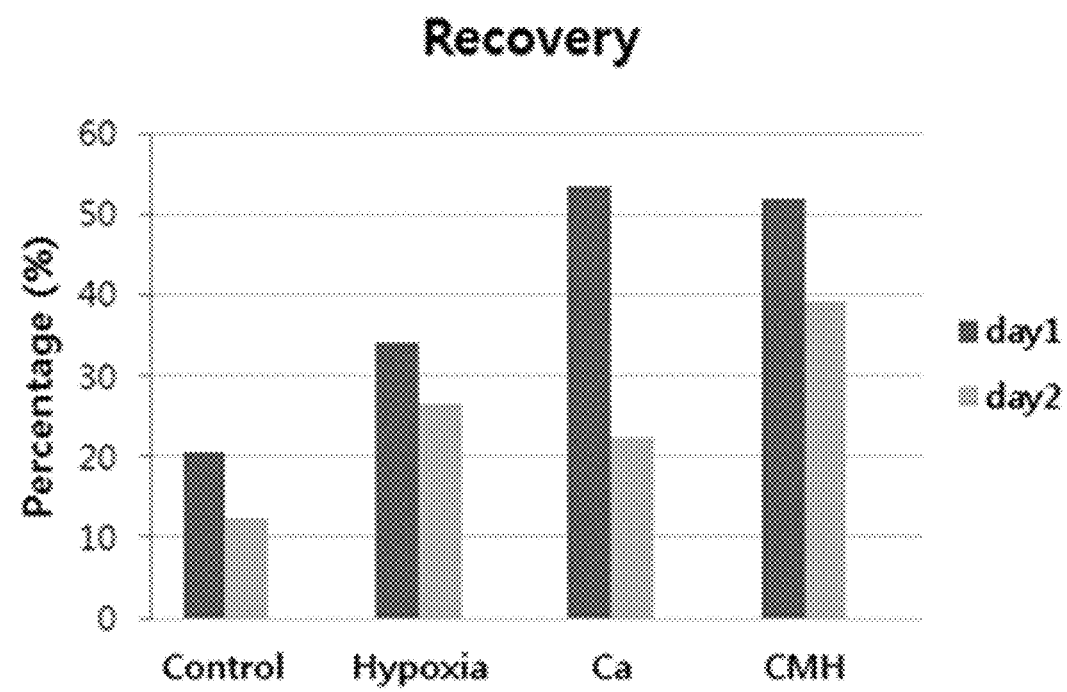

As can be seen in FIG. 5A and FIG. 5B, the cells were observed to exhibit higher viability and recovery rate when they were cultured in a hypoxic condition or an increased calcium condition than in a typical condition, and even higher viability and recovery rate when they were cultured in the CMH condition. The same results were obtained with umbilical cord blood-derived mesenchymal stem cells derived from different sources although there were a difference therebetween to some degree. These data, taken together, indicate that the CMH condition is advantageous over a typical condition, or the individual conditions, in increasing the viability of umbilical cord blood-derived mesenchymal stem cells to recover a greater number of cells.

Figure 6A:
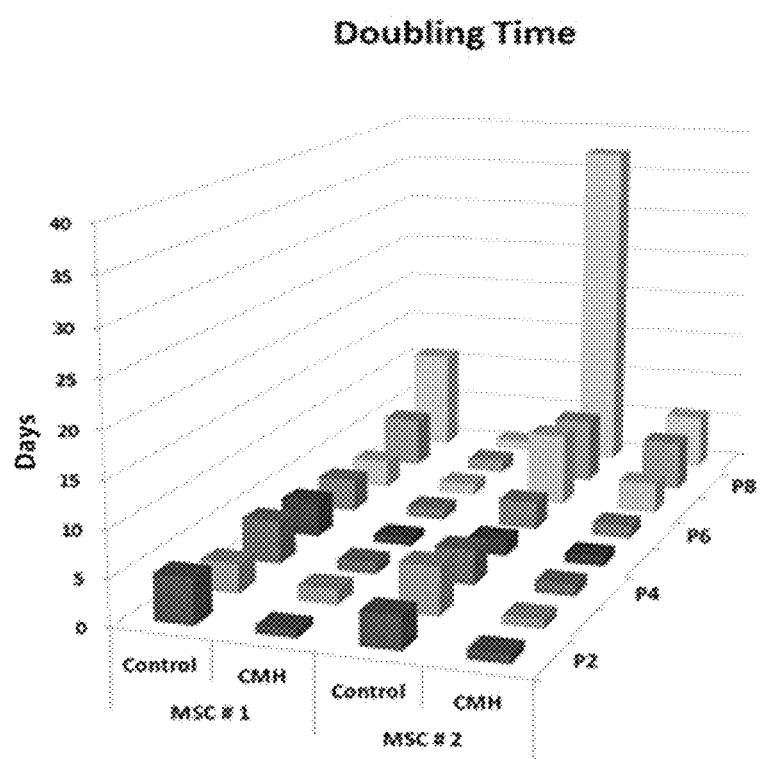
FIG. 6A, FIG. 6B, FIG. 6C, and FIG. 6D show doubling times (FIG. 6A and FIG. 6C), and cumulative cell counts (FIG. 6B and FIG. 6D) after umbilical cord blood-derived mesenchymal stem cells (MSC #1 to #4) were cultured in a typical condition (control), and in a CMH condition. In each of FIGS. 6A-6D graph, P1 to P9 represent numbers of passage.
Figure 6B:
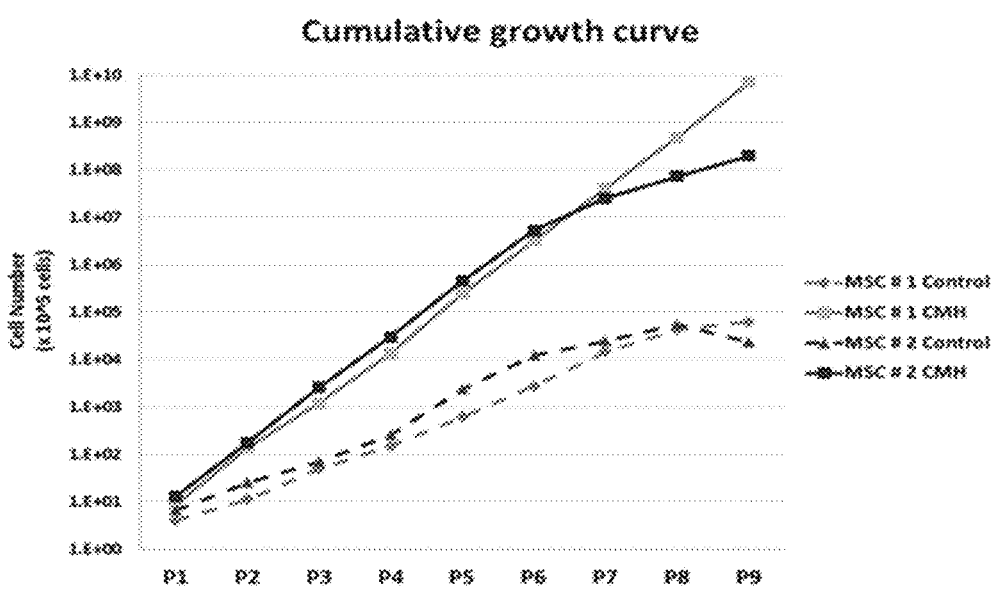
Figure 6C:
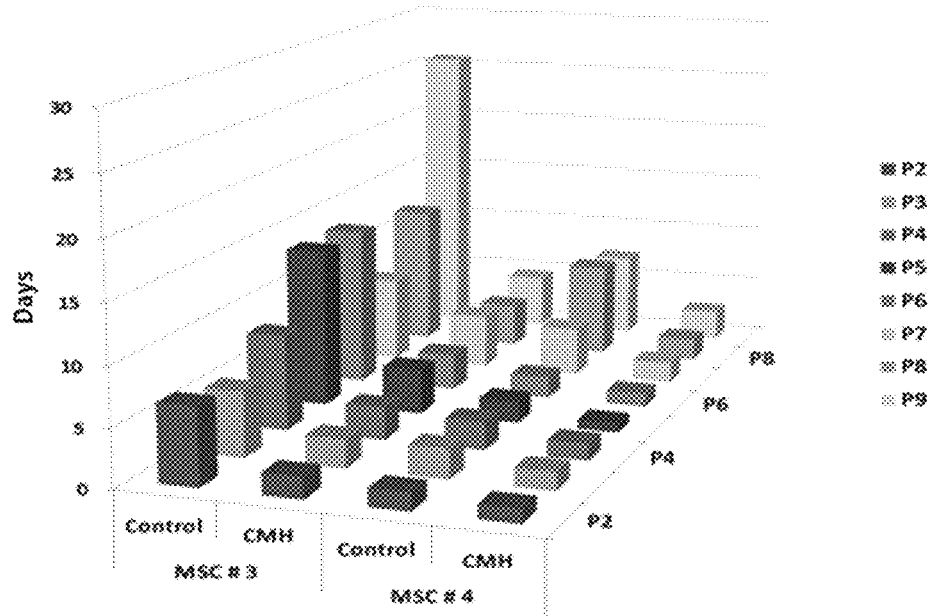
Figure 6D:
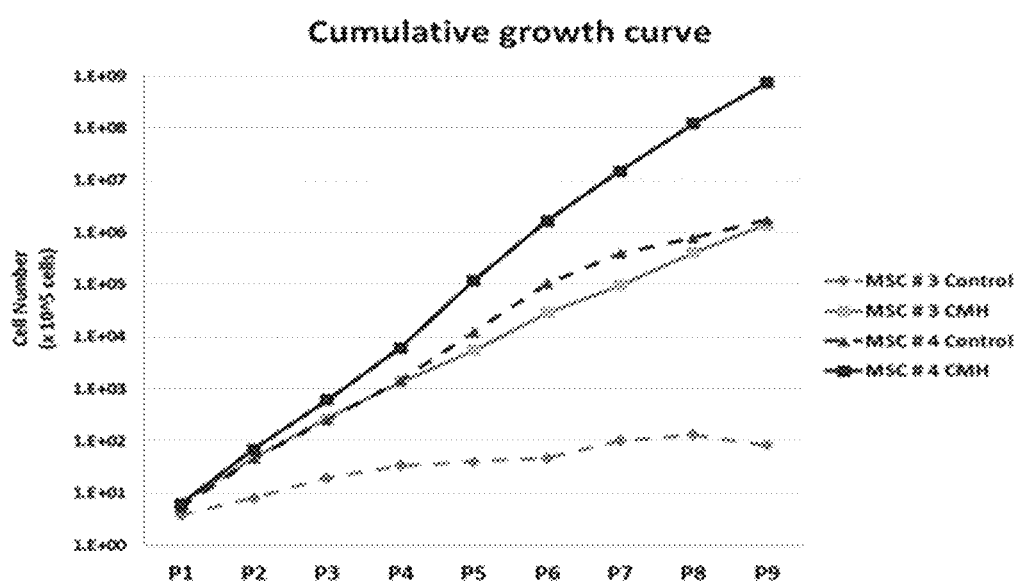

Mesenchymal stem cells (MSC #1 to #4) were cultured with passage in a typical condition and in the CMH condition, and examined for proliferative capacity. The results are given in FIG. 6A through FIG. 6D which show doubling time (FIG. 6A and FIG. 6C) and cumulative cell counts (FIG. 6B and FIG. 6D).

As can be seen in the graphs, the CMH condition significantly reduced the doubling time, an index for cell proliferation, over many rounds of passage, compared to the control. In addition, as is apparent from the data of the cumulative growth curves, a much greater number of mesenchymal stem cells, even though derived from the same source, were obtained in the CMH condition. The same results were obtained from experiments with different umbilical cord blood-derived mesenchymal stem cells although there was a difference therebetween to some degree. These data indicate that the CMH condition induces mesenchymal stem cells to proliferate with better efficiency. Particularly, an even greater number of mesenchymal stem cells were produced when the CMH condition was applied to an initial passage of umbilical cord blood-derived mesenchymal stem cells.

Example 5: Assay for Stemness and Senescence of Umbilical Cord Blood-Derived Mesenchymal Stem Cells According to Culture Condition To examine why the CMH condition improves the proliferation of umbilical cord blood-derived mesenchymal stem cells, their stemness and senescence, which are associated with the proliferation of stem cells, were assayed.

For this, umbilical cord blood-derived mesenchymal stem cells were cultured in a typical condition and in the CMH condition, as in Example 3. The cells were detached with trypsin when they reached 80-90% confluency. After removal of the media by centrifugation, the cells were washed with PBS and recovered by centrifugation. This procedure was repeated twice to completely remove media from the cells. Subsequently, RNA was isolated using an RNA isolation kit (Invitrogen) according to the protocol of the manufacturer. The RNA was reverse transcribed into cDNA in the presence of the reverse transcriptase SuperScript™III (Invitrogen). Real-time PCR was carried out on the cDNA using primers specific for the stemness markers Oct4 and nanog, the senescence marker P16, and GADPH. The PCR started with denaturation at 95° C. for 10 min, and was performed with 30 cycles of 95° C. for 10 sec, 62° C. for 30 sec, and 72° C. for 10 sec in a LIGHTCYCLER® 480 Real-Time PCR System instrument (Roche).

TABLE 1

Primers for RT-PCR

| Marker | Sequence (F: forward, R: reverse) |
|---|---|
| Oct4 | F; CAATTTGCCAAGCTCCTGA (SEQ ID NO: 1)<br>R; CGTTTGGCTGAATACCTTCC (SEQ ID NO: 2) |
| Nanog | F; AGATGCCTCACACGGAGACT (SEQ ID NO: 3)<br>R; TTTGCGACACTCTTCTCTGC (SEQ ID NO: 4) |
| P16 | F; GTGGACCTGGCTGAGGAG (SEQ ID NO: 5)<br>R; CTTTCAATCGGGGATGTCTG (SEQ ID NO: 6) |
| GADPH | F; AGCCACCATCGCTCAGACAC (SEQ ID NO: 7)<br>R; GCCCAATACGACCAAATCC (SEQ ID NO: 8) |

The levels of RNA obtained by the RT-PCR were normalized to that of GAPDH before the expression levels of RNA for each marker in the cells cultured in the typical condition and the CMH condition were compared (relative analysis, ddCT method).

Figure 7A:
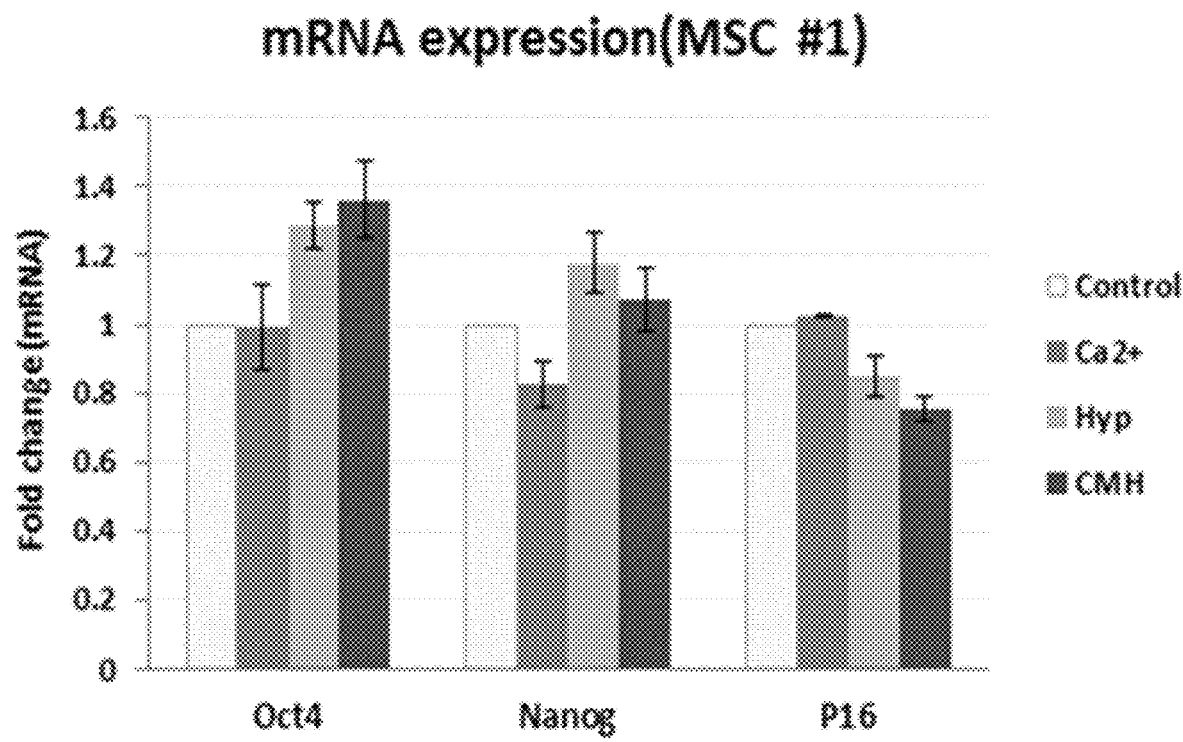
FIG. 7A and FIG. 7B show mRNA expression levels of the stemness markers Oct4 and nanog and the senescence marker P16 after umbilical cord blood-derived mesenchymal stem cells derived from two different sources (MSC #1 and #2) were cultured in a typical condition (control), in a calcium addition condition (Ca2+), in a hypoxic condition, and in a CMH condition.
Figure 7B:
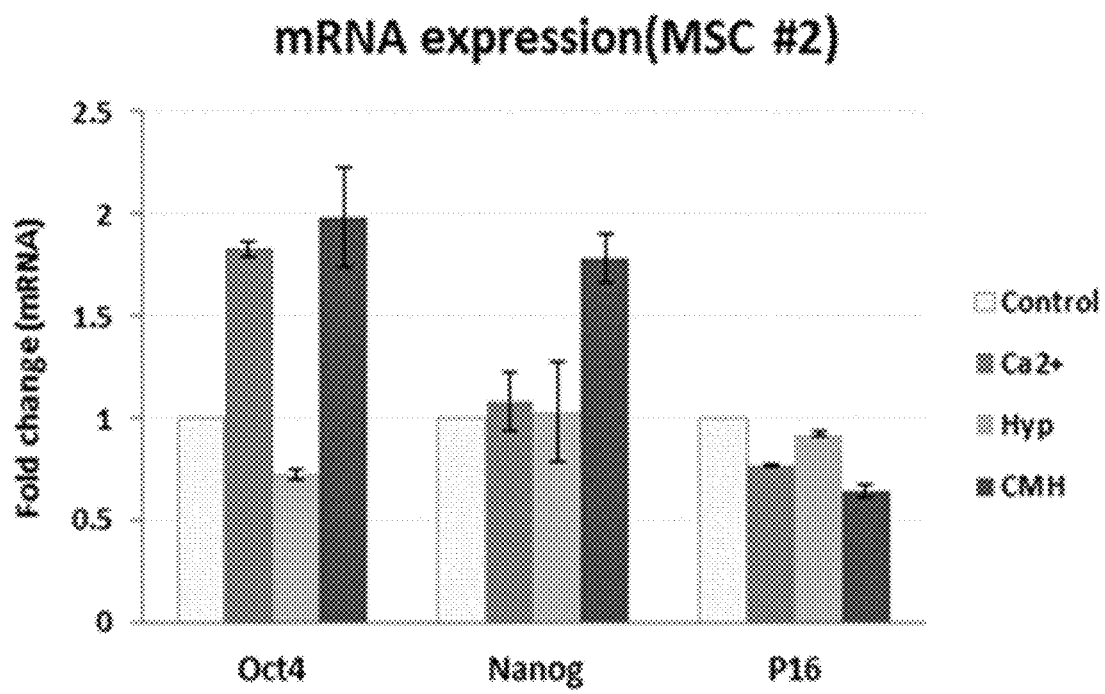

The results are given in FIG. 7A and FIG. 7B. FIG. 7A and FIG. 7B show mRNA expression levels of two different umbilical cord blood-derived mesenchymal stem cells (MSC #1 and #2).

As can be seen in FIG. 7A and FIG. 7B, the expression levels of the stemness markers Oct4 and nanog were higher in the umbilical cord blood-derived mesenchymal stem cells cultured in the CMH condition than in a typical condition (control) and than in individual conditions. The senescence marker P16 showed an inverse expression pattern to that of Oct4. These results indicate that the CMH condition maintains the stemness of mesenchymal stem cells while suppressing the senescence, thus improving proliferative capacity.

To confirm the ability of the CMH condition to suppress the senescence of mesenchymal stem cells, the following experiments were carried out. Umbilical cord blood-derived mesenchymal stem cells were cultured in a typical condition and in the CMH condition as in Example 3, with 7-8 passages. After removal of the media, the cells were washed once with PBS, and incubated at room temperature for 3-5 min with 1 mL of a 1× fixation solution (Cell Signaling Technology). The fixation solution was removed from the cells which were then washed twice with 2 mL of PBS. Subsequently, the cells were incubated for 2 to 24 hrs with 1 mL of a dye solution for β-galactosidase (Cell Signaling Technology) in a 37° C. incubator. After removal of the dye solution therefrom, the cells were washed with 1 mL of PBS, and the resulting stained senescent cells were counted under the inverted microscope ECLIPSE TE2000-U (Nikon Co., Kanagawa, Japan).

Figure 8A:
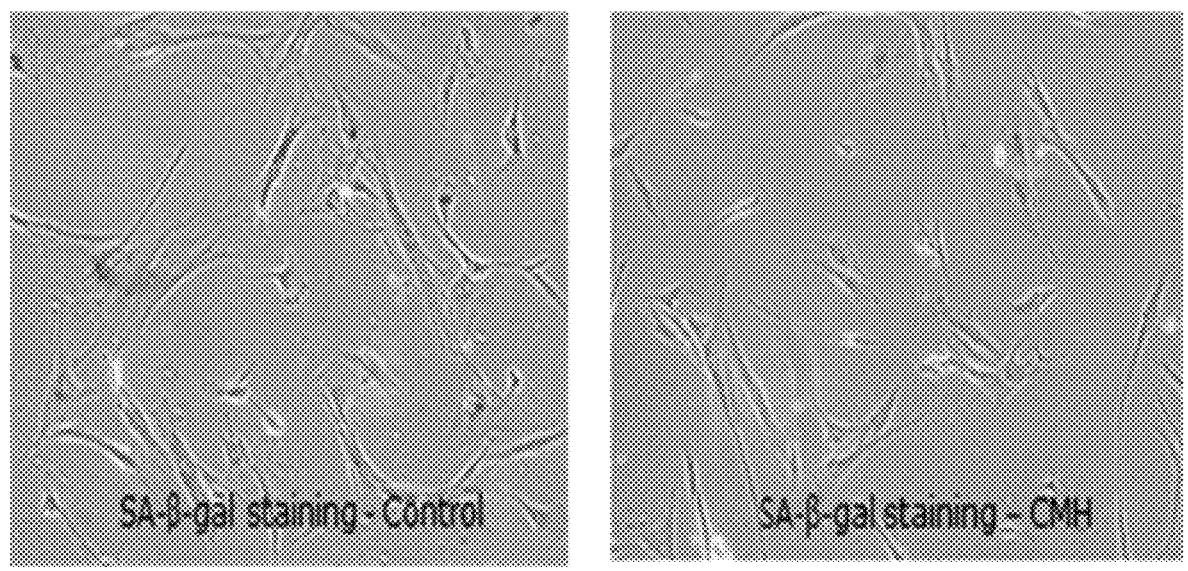
FIG. 8A and FIG. 8B show photographs of umbilical cord blood-derived mesenchymal stem cells stained with SA-β-gal after passages in a typical condition (control) and in a CMH condition (FIG. 8A), and a graph in which β-gal activity is plotted according to culture conditions after umbilical cord blood-derived mesenchymal stem cells were cultured in a typical condition (control), in a calcium addition condition ($Ca^{2+}$), in a hypoxic condition, and in a CMH condition (FIG. 8B).
Figure 8B:
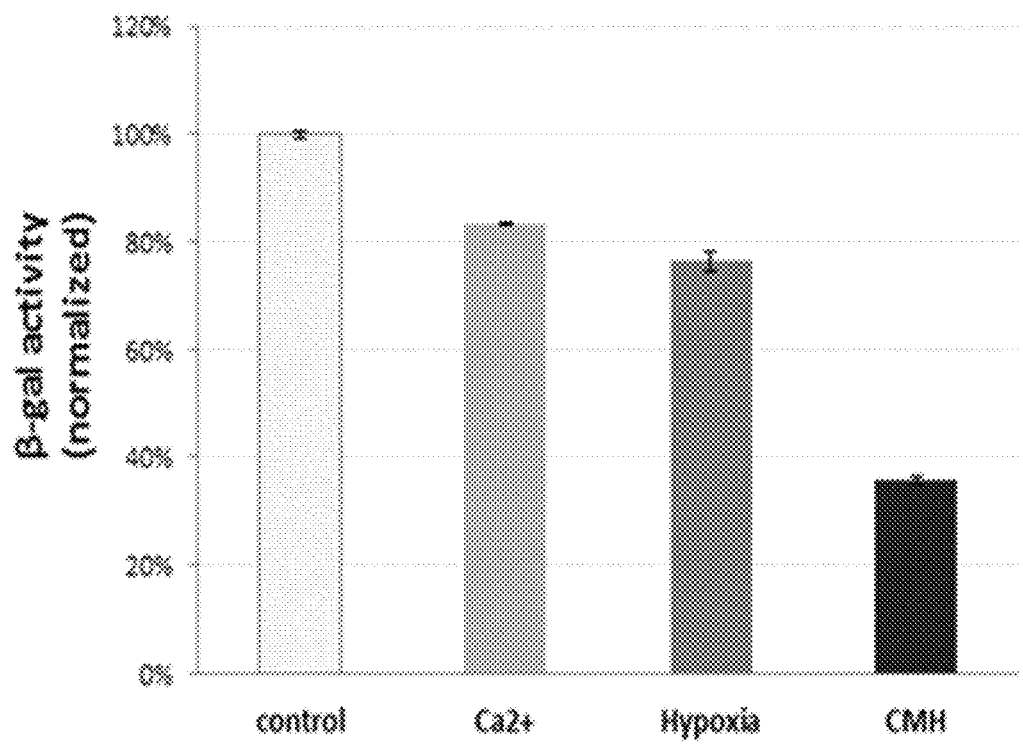

The results are given in FIG. 8A and FIG. 8B. FIG. 8A and FIG. 8B show microphotographs of cells after staining with SA-β-gal (FIG. 8A), and graphs of SA-β-gal activity (FIG. 8B). The SA-β-gal activity was determined by calculating the ratio of stained cells to total cells counted on a photograph taken at 40--100-fold magnification As is apparent from FIG. 8A and FIG. 8B, the progression of senescence in the mesenchymal stem cells was retarded further in the CMH condition than in the calcium addition condition or the hypoxic condition, and much further than in the typical condition.

Taken together, the data obtained above demonstrate that the CMH condition of the present invention maintains stemness and suppresses senescence more efficiently than do the typical conditions or the individual conditions, whereby the mesenchymal stem cells can proliferate with high efficiency.

Example 6: Differentiation Potential and Maker Expression of Umbilical Cord Blood-Derived Mesenchymal Stem Cells According to Culture Condition An examination was made of the effect of the CMH condition on the property of umbilical cord blood-derived mesenchymal stem cells. To this end, mesenchymal stem cells were assayed for differentiation potential and marker expression by chondrogenic induction and osteogenic induction.

Umbilical cord blood-derived mesenchymal stem cells obtained from two different sources (MSC #1 and #2) were cultured in a typical condition (control) and in the CMH condition, as in Example 3, before they were induced to differentiate into cartilage and bone, as follows. Then, differentiation into cartilage and bone was evaluated using a staining method.

Chondrogenic Induction

For use in chondrogenic induction, cells were placed in a population of $2-2.5\times10^5$ cells in a 15 mL conical tube, and centrifuged to give a cell pellet. It was washed with D-PBS and suspended in 200-250 μl of a differentiation medium [high glucose DMEM (Gibco, cat #. 11995), 10 ng/ml TGFβ-3 (Sigma, cat #. T5425, 2 μg), 500 ng/ml BMP-6 (R&D, cat #. 507-BP, 20 μg), 50 μg/ml ascorbic acid (Sigma, cat #. A8960), 50 mg/ml (1:100) ITS™+Premix (BD, cat #. 354352), 40 μg/ml L-proline (Sigma, cat #. P5607), 100

μg/ml sodium pyruvic acid (Sigma, cat #. P8574), 100 nM dexamethasone (Sigma, cat #. D2915)], and the cell suspension was aliquoted into tubes. These tubes were centrifuged at 1,500 rpm for 5 min, after which the cells were cultured for 4 weeks in a 37° C. $CO_2$ incubator, with the tubes opened slightly, to induce differentiation into cartilage. The differentiation medium was substituted by half with a fresh one, twice a week.

Cartilage Staining Protocol

After the chondrogenic induction, the cells were centrifuged, washed with PBS, and fixed at room temperature for 0.5 to 1 hr in 4% paraformaldehyde. Subsequently, the cells were washed two or three times with distilled water, and prepared into sections (4-5 μm thick) using a cryosection method. The sections were immersed for 3-5 min in 95% ethanol, and washed twice with water. After being stained for 7 min with 0.1% safranin 0, the cells were washed twice with 70% ethanol, once with 70% ethanol, twice with 95% ethanol, once with 95% ethanol, and twice with 100% ethanol, immersed for 3 min in a xylene substrate solution, and dried. Thereafter, the stained cells were covered with a lipid-soluble mounting solution and observed. The chondrogenic induction was evaluated by comparing the color (violet), the size of differentiated pellets, and the lacuna structure formed.

Osteogenic Induction

For use in osteogenic induction, the cells were plated at a density 500-1000 cells/well into 6-well plates, and 2~4 days later, the medium was substituted with an osteogenic induction medium (β-glycerol phosphate 2.1604 g, L-ascorbic acid-2-phosphate 0.012805 g, dexamethasone/UVAB 0.6 mg, gentamycin (10 mg/ml) 5 ml and FBS 100 ml in 1 L of α-MEM). The cells were cultured for 2-3 weeks with the differentiation medium substituted with a fresh one every three days. The chondrogenic induction was evaluated by an ALP staining method.

Bone Staining Protocol

The differentiated cells were washed twice with PBS and incubated for 30~45 sec in a fixation solution (40% acetone). They were washed again two or three times with distilled water and incubated for 30 min with an alkaline staining solution (Fast violet B salt) in a dark place. Then, the cells were washed twice with distilled water, and treated for 10-20 sec with Mayer's hematoxylin solution. After removal of the staining solution therefrom, the cells were washed with tap water, dried, covered with a lipid-soluble mounting solution, and observed. Because osteoblasts are stained dark brown due to the activation of intracellular alkaline phosphatase, the chondrogenic induction was evaluated by the degree of staining.

Figure 9A:
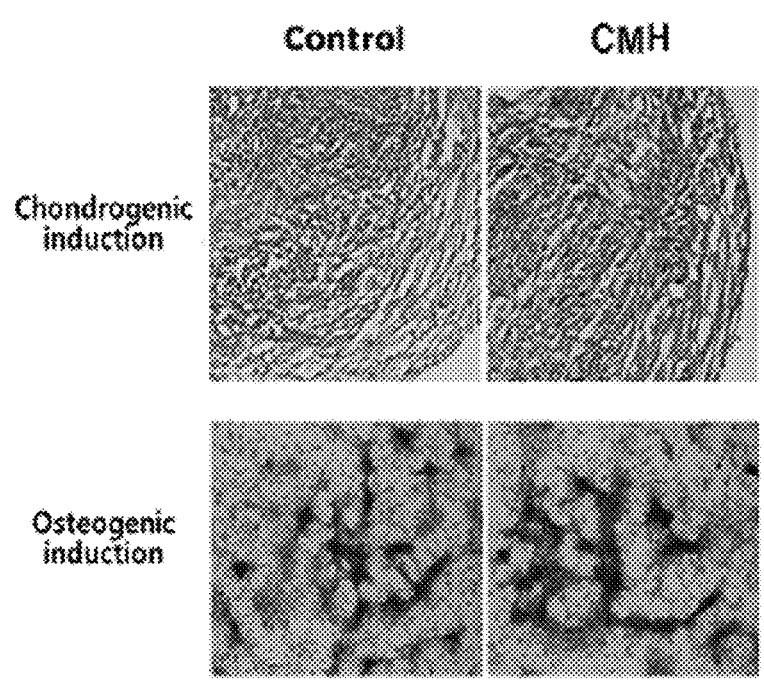
FIG. 9A and FIG. 9B show photographs of umbilical cord blood-derived mesenchymal stem cells derived from two different sources (MSC #1 and #2) after the cells cultured in a typical condition (control) and in a CMH condition were induced to differentiate to cartilage and bone.
Figure 9B:
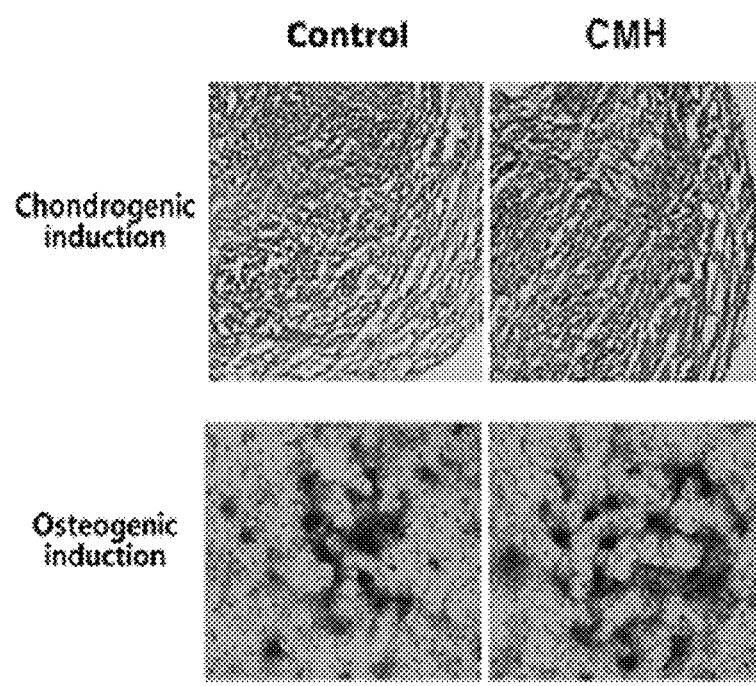

The results are given in FIG. 9A and FIG. 9B. As can be seen in FIG. 9A and FIG. 9B, there were no significant differences in chondrogenic induction and genic induction between the mesenchymal stem cells cultured in the typical condition and in the CMH condition.

Meanwhile, immunophenotypes of the cell surface antigens on the umbilical cord blood-derived mesenchymal stem cells cultured according to the method of the present invention were examined. In this context, the expression of the surface markers (CD34, CD73, CD45, and CD105) was analyzed using FACS.

Umbilical cord blood-derived mesenchymal stem cells cultured in a typical condition and in the CMH condition were trypsinized, and washed three times with PBS containing 2% FBS. They were reacted with the hematopoietic cell-associated antigens CD34 and CD45, both conjugated with FITC (fluorescein isothiocyanate), the immunomodulation-associated antigen CD73 conjugated with PE (phycoerythrin), and the angiogenesis-associated antigen CD105 conjugated with PE. Afterwards, the cells were additionally marked with a secondary antibody (IgG-FITC; Jackson ImmunoResearch, West Grove, Pa., USA) in a manner similar to Western blotting, followed by detecting the signal of the secondary antibody using FACS to ratios of the cells expressing the markers to total cells. After the reaction, the signals were analyzed using a FACSCALIBUR™ flow cytometer (Becton Dickinson, San Jose, Calif., USA), and the software CELLQUEST.

The results are summarized in Table 2, below.

TABLE 2

|  |  | CD34 | CD73 | CD45 | CD105 |
|---|---|---|---|---|---|
| MSC #1 | Control | − | + | − | + |
|  | CMH | − | + | − | + |
| MSC #2 | Control | − | + | − | + |
|  | CMH | − | + | − | + |
| MSC #3 | Control | − | + | − | + |
|  | CMH | − | + | − | + |

As is understood from the data of Table 2, there were no significant differences in the expression of marker proteins between cells cultured in the CMH condition and in the typical condition.

Taken together, the data obtained above demonstrate that the CMH condition of the present invention has no significant influence on the fundamental properties of umbilical cord blood-derived mesenchymal stem cells.

Example 7: Comparison of Immunogenicity and Immunosuppression of Umbilical Cord Blood-Derived Mesenchymal Stem Cells According to Culture Condition Immunological properties of umbilical cord blood-derived mesenchymal stem cells according to culture conditions were evaluated using a mixed lymphocyte reaction (MLR) as follows.

For a negative control, umbilical cord blood-derived mesenchymal stem cells cultured in the presence of 10 μg/ml mitomycin C (Sigma-Aldrich, St Louis, Mo., USA) in a typical condition and in the CMH condition were separately seeded at a density of $2 \times 10^4$ cells/well into 96-well plates, responding cells (peripheral blood monocytes (expressed as "A"); ALLCELLS, Emeryville, Calif.) at a density of $1 \times 10^5$ cells/well, and stimulator cells (unrelated peripheral blood monocytes (expressed as "B"); ALLCELLS, Emeryville, Calif.) at a density of $1 \times 10^5$ cells/well. As a positive control (1), peripheral blood monocytes treated with 10 μg/ml PHA-L (expressed as "H"; Roche Diagnostics GmbH, Mannheim, Germany) were added at a density of $1 \times 10^5$ cells/well to 96-well plates. For a positive control (2), each of the responding cells and the stimulator cells were added at a density of $1 \times 10^5$ cells/well. In a test group, mesenchymal stem cells were incubated with peripheral blood monocytes, PHA-L-stimulated peripheral blood monocytes, or a combination of the responding cells and the stimulator cells, each monocyte being used at a density of $1 \times 10^5$ cells, for 5 days, and the proliferation and colony formation of the responding cells were observed under a microscope. On day 5 after incubation, the cells were treated with BrdU (BD Bioscience, San Jose, Calif., USA) so that levels of the DNA newly synthesized for the previous 24 hrs in the responding cells were determined by measuring absorbance at 370 nm on a VERSAmax™ microplate reader (Molecular Devices Co., Sunnyvale, Calif., USA).

Figure 10A:
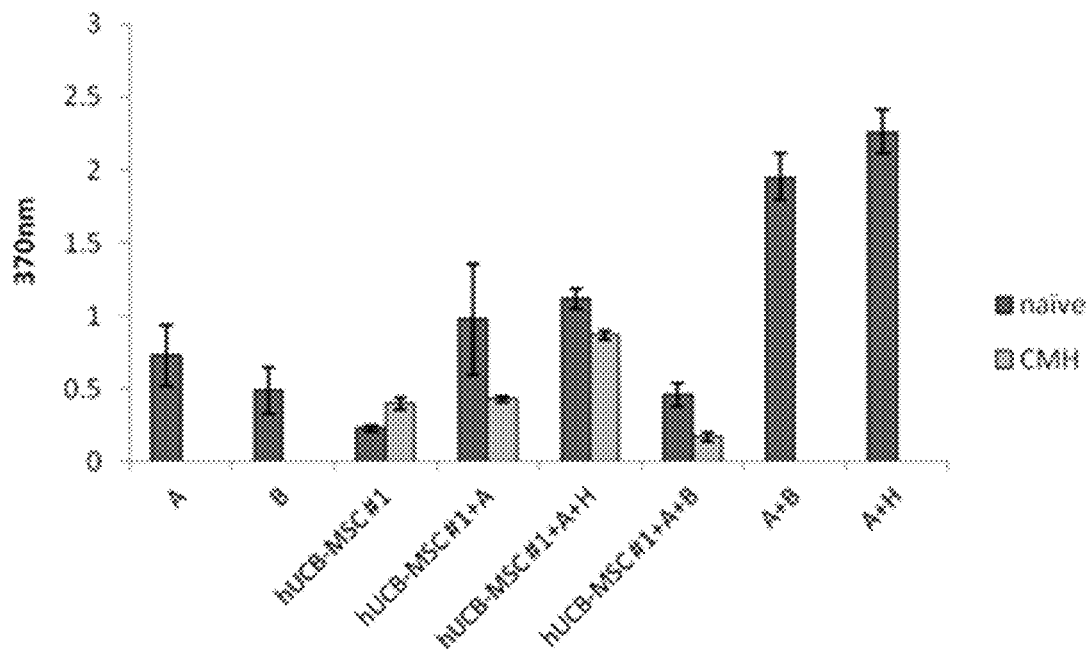
FIG. 10A and FIG. 10B show graphs illustrating whether two different umbilical cord blood-derived mesenchymal stem cells (MSC #1 and #2) cultured in a typical condition (control) and in a CMH condition stimulate responding cells (A), wherein A, B and H represent responding cells, stimulator cells, and PHA, respectively.
Figure 10B:
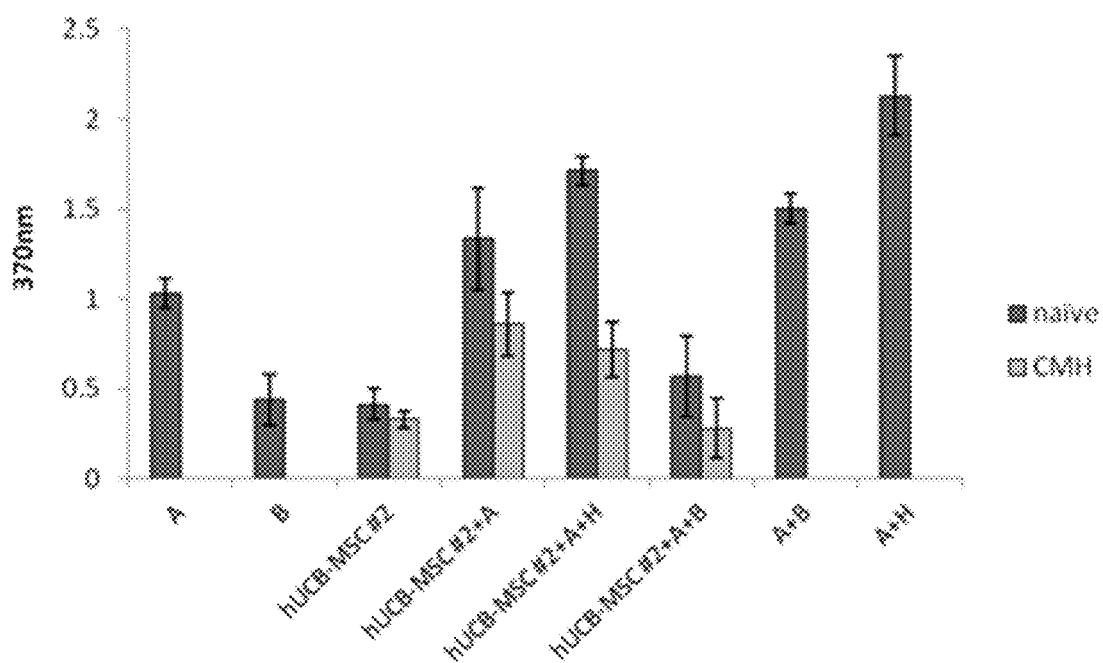

The results are shown in FIG. 10A and FIG. 10B. As can be seen in FIG. 10A and FIG. 10B, the proliferation was induced in the PHA-L(H)-stimulated unrelated peripheral blood monocytes (A+H) whereas umbilical cord blood-derived mesenchymal stem cells did not stimulate the responding cells, thus resulting in no induction of cell proliferation (hUCB-MSC+A). Particularly, the umbilical cord blood-derived mesenchymal stem cells were observed to have greater inhibitory effects on the proliferation of the responding cells when they were cultured in the CMH condition than in a typical condition. These data indicate that the umbilical cord blood-derived mesenchymal stem cells cultured in the CMH are less apt to be immunogenic than are those cultured in a typical condition.

When applied to the situation in which the immune response was induced by a reaction between the responding cells (A) and the stimulator cells (B), i.e., (A+B), or by the artificial stimulation of the responding cells (A) with PHA-L, i.e., (A+H), the umbilical cord blood-derived mesenchymal stem cells cultured in the CMH condition were observed to suppress the proliferation of the responding peripheral blood monocytes more greatly than did those cultured in the typical condition. Similar results were obtained with umbilical cord blood-derived mesenchymal stem cells obtained from different sources although there was a difference to some, but slight degree. These data demonstrate that the CMH culture condition is advantageous over typical conditions in terms of the suppression of immunogenicity.

After the mesenchymal stem cells were reacted in the same manner as described above, $PGE_2$ (prostaglandin $E_2$), an immunosuppressant, released therefrom was analyzed using a PGE2 ELISA kit (Cayman, Ann Arbor, Mich., USA) according to the protocol of the manufacturer. The cultures from the MLR were used as specimens.

Standards necessary for ELISA assay were prepared to have a maximum density of 1,000 pg/mL, with a minimum density of 7.8 pg/mL serially half-diluted from the maximum. Each of the standards and the culture supernatants of the test group was added in an amount of 50 µl to each well of $PGE_2$ capture antibody-coated plates. Then, 50 µl of the $PGE_2$ AchE tracer and 50 µl of a primary antibody were added to each well, followed by incubation at 4° C. for 18 hrs. The plates were washed five times with a wash buffer, and 200 µl of Ellman's reagent (included within the kit), was added to each well, followed by the addition of 5 µl of the tracer per well. The plates were incubated for 60-90 min in a dark condition, and absorbance was read at 450 nm.

Figure 11A:
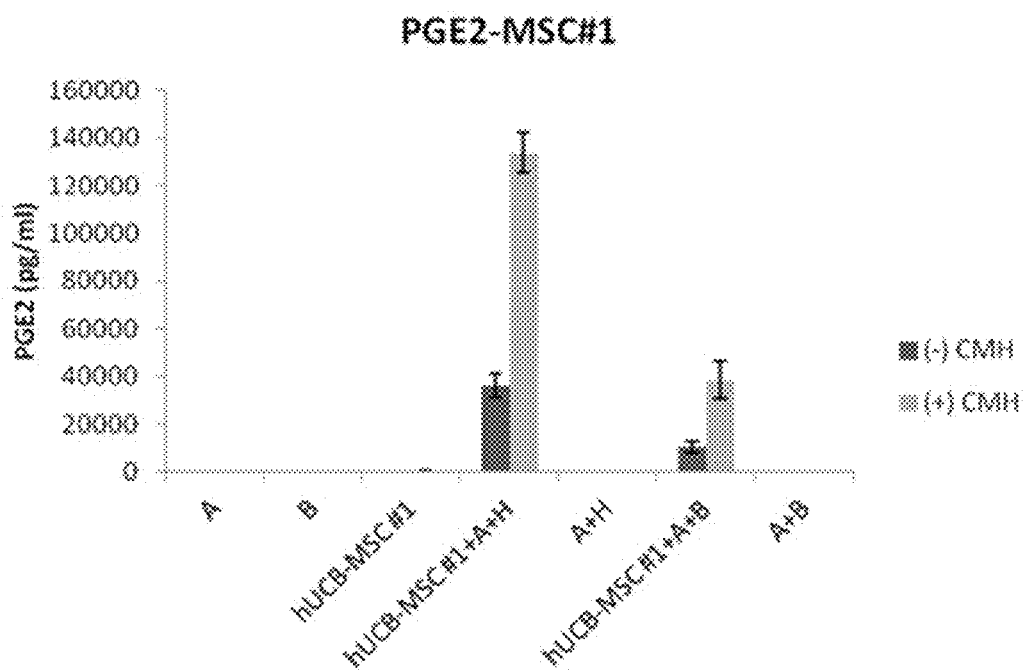
FIG. 11A and FIG. 11B show graphs of levels of $PGE_2$ (prostaglandin $E_2$) released from umbilical cord blood-derived mesenchymal stem cells (MSC #1 and #2) cultured in the conditions of FIG. 10A and FIG. 10B.
Figure 11B:
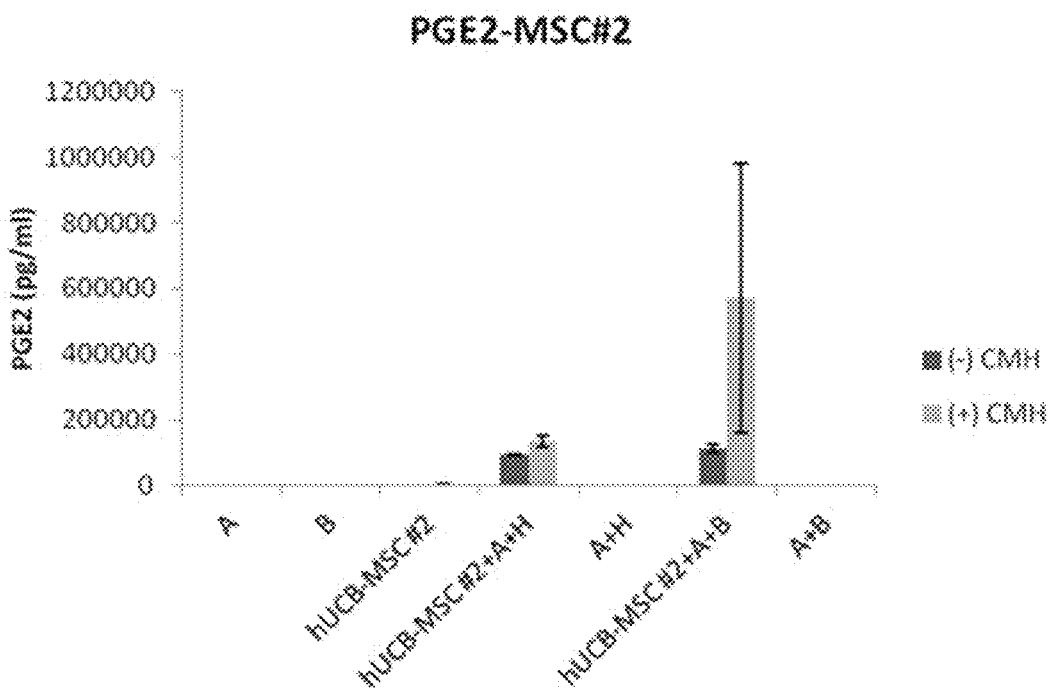

The results are given in FIG. 11A and FIG. 11B. As can be seen in FIG. 11A and FIG. 11B, the umbilical cord blood-derived mesenchymal stem cells were observed to release $PGE_2$ in an approximately 3.7-fold greater amount when cultured in the CMH condition than in a typical condition. Similar results were obtained with different umbilical cord blood-derived mesenchymal stem cells. These data demonstrate that the umbilical cord blood-derived mesenchymal stem cells cultured in the CHM condition were more immunosuppressant than those cultured in a typical condition.

Example 8: In Vitro Assay for Ability of Umbilical Cord Blood-Derived Mesenchymal Stem Cells to Release Cytokines According to Culture Condition Effects of culture conditions on the ability of umbilical cord blood-derived mesenchymal stem cells to release cytokines were assayed by measuring Tsp-2 released during the differentiation of the umbilical cord blood-derived mesenchymal stem cells into chondrocytes.

Umbilical cord blood-derived mesenchymal stem cells were cultured in a typical condition (control) and in the CMH condition in the same manner as in Example 3. When reaching 80-90% confluency, they were detached by treatment with trypsin. After centrifugation, the cell pellets were washed with high glucose DMEM containing 40 µg/ml L-proline, 0.6 µg/ml dexamethasone, 50 µg/ml ascorbic acid, and 100 µg/ml sodium pyruvate, to completely remove FBS from the cells. The umbilical cord blood-derived mesenchymal stem cell pellets obtained again by centrifugation were suspended at a density of $2.0 \times 10^5$ cells/400 µl, and placed in an aliquot of 400 µl in 15 mL conical tubes. Following centrifugation at 550×g for 5 min, the tubes were so very loosely closed. The tubes were incubated for 24 hrs while being placed upright in a rack. Once a pellet was formed, the supernatant was collected and analyzed for the level of Tsp-2 using a Tsp-2 assay kit (R&D systems, USA).

Figure 12:
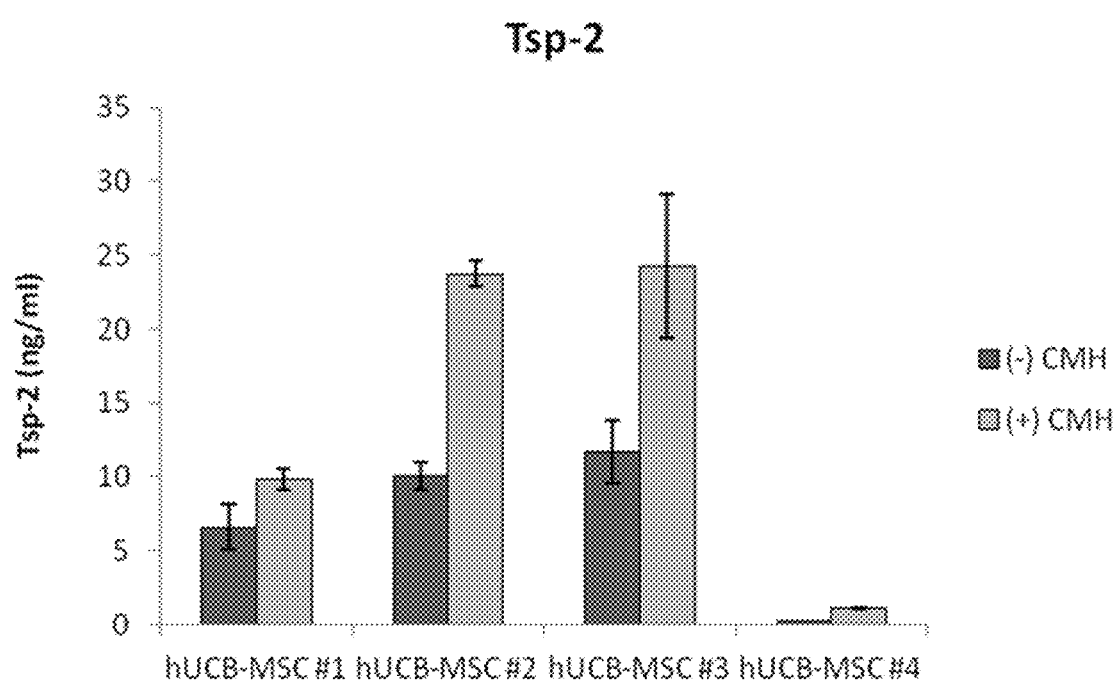
FIG. 12 is a graph showing levels of Tsp-2 released from four different umbilical cord blood-derived mesenchymal stem cells (MSC #1 to #4) cultured for 24 hrs in a typical condition (control) and in a CMH condition.

The results are given in FIG. 12. Tsp-2 is a factor accounting for the titer of umbilical cord blood-derived mesenchymal stem cells for use as a cartilage regenerating agent. Cells that released a higher level of Tsp-2 were evaluated to regenerate cartilage more effectively. As is apparent from the data of FIG. 12, all of four different umbilical cord blood-derived mesenchymal stem cells released higher levels of Tsp-2 in the CMH condition than in a typical condition.

Taken together, the data obtained above indicate that the umbilical cord blood-derived mesenchymal stem cells cultured in the CMH condition have excellent potential of differentiating into chondrocytes and are thus useful as a cartilage regenerating agent.

What is claimed is:

1. A method for treating or improving a pulmonary disease, comprising administering a cell therapeutic agent comprising mesenchymal stem cells to a subject in need thereof,
   wherein said mesenchymal stem cells are obtained by a culture method comprising:
   (a) culturing mesenchymal stem cells in a medium containing calcium in a concentration of from 2.7 to 3.8 mM and magnesium in a concentration of from 1.0 to 3.0 mM under a hypoxic condition of 2 to 5% oxygen.

2. The method of claim 1, wherein the mesenchymal stem cells of (a) are derived from umbilical cord blood, bone marrow, lipid, muscle, skin, amniotic fluid, umbilical cord, or teeth.

3. The method of claim 1, wherein the medium is selected from the group consisting of a Dulbecco's modified eagle medium (DMEM), a minimal essential medium (MEM), an α-MEM, a McCoys 5A medium, an eagle's basal medium, a CMRL (Connaught Medical Research Laboratory) medium, a Glasgow MEM, a Ham's F-12 medium, an Iscove's modified Dulbecco's medium (IMDM), a Leibovitz's L-15 medium, an Roswell Park Memorial Institute (RPMI) 1640 medium, a medium 199, and a Hank's medium 199.

4. The method of claim 3, wherein the medium comprises 5 to 30% of fetal bovine serum.

5. The method of claim 3, wherein the medium does not comprise fetal bovine serum, but a serum replacement.

6. The method of claim 1, wherein the medium is based on an α-MEM supplemented with 5 to 30% of fetal bovine serum (FBS), 0.3 to 2.0 mM of calcium, and 0.2 to 2.2 mM of magnesium.

7. The method of claim 1, wherein the culture method further comprises sub-culturing the mesenchymal stem cells obtained in (a) in the same condition as in claim 1.

8. The method of claim 1, wherein the medium of (a) comprises calcium in a concentration of from 3.3 to 3.8 mM.

* * * * *